(12) United States Patent
Tang et al.

(10) Patent No.: US 6,545,127 B1
(45) Date of Patent: Apr. 8, 2003

(54) CATALYTICALLY ACTIVE RECOMBINANT MEMAPSIN AND METHODS OF USE THEREOF

(75) Inventors: Jordan J. N. Tang, Edmond, OK (US); Xinli Lin, Edmond, OK (US); Gerald Koelsch, Oklahoma City, OK (US); Lin Hong, Oklahoma City, OK (US)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 0 days.

(21) Appl. No.: 09/604,608

(22) Filed: Jun. 27, 2000

Related U.S. Application Data

(60) Provisional application No. 60/141,363, filed on Jun. 28, 1999, provisional application No. 60/168,060, filed on Nov. 30, 1999, provisional application No. 60/177,836, filed on Jan. 25, 2000, provisional application No. 60/178,368, filed on Jan. 27, 2000, and provisional application No. 60/210, 292, filed on Jun. 8, 2000.

(51) Int. Cl.$^7$ .................. G01N 33/48; G01N 31/00; G06F 19/00; A16K 38/00; C07K 1/00; C07K 14/00; C07K 17/00; C07M 21/02; C07M 21/04

(52) U.S. Cl. ................ 530/350; 702/19; 530/300; 536/23.1

(58) Field of Search ............... 435/212, 183, 435/7.1, 226, 15; 530/300; 536/350, 23.1; 702/19, 27

(56) References Cited

U.S. PATENT DOCUMENTS

| 4,923,967 A | * | 5/1990 | Bobbitt et al. | 530/351 |
|---|---|---|---|---|
| 5,200,339 A | | 4/1993 | Abraham | 435/212 |
| 5,221,607 A | | 6/1993 | Cordell et al. | 435/6 |
| 5,235,043 A | * | 8/1993 | Collins et al. | 530/399 |
| 5,252,463 A | | 10/1993 | Nelson et al. | 435/23 |
| 5,733,768 A | | 3/1998 | Dixon et al. | 435/226 |
| 5,744,346 A | | 4/1998 | Chrysler et al. | 435/226 |
| 5,942,400 A | | 8/1999 | Anderson et al. | 435/7.1 |
| 5,978,740 A | | 11/1999 | Armistead | 702/19 |
| 5,986,054 A | | 11/1999 | George-Hyslop et al. | 530/350 |
| 6,077,682 A | | 6/2000 | Inouye et al. | 435/15 |
| 6,245,884 B1 | | 6/2001 | Hook | 530/300 |
| 6,313,268 B1 | | 11/2001 | Hook | 530/350 |
| 6,329,163 B1 | | 12/2001 | Anderson et al. | 435/23 |
| 6,420,534 B1 | | 6/2002 | Gurney et al. | 530/827 |

FOREIGN PATENT DOCUMENTS

| EP | 0 302 469 A2 | 2/1989 |
|---|---|---|
| EP | 0 855 444 A2 | 7/1998 |
| JP | 10 108 681 A | 4/1998 |
| WO | WO96/40885 A2 | 12/1996 |
| WO | WO97/27296 A1 | 7/1997 |
| WO | WO98/13488 A2 | 4/1998 |
| WO | WO98/15828 A1 | 4/1998 |
| WO | WO98/21589 A1 | 5/1998 |
| WO | WO98/26059 A1 | 5/1998 |
| WO | WO99/64587 A1 | 12/1999 |
| WO | WO00/17369 A3 | 3/2000 |
| WO | WO00/23576 A3 | 4/2000 |
| WO | WO00/47618 A2 | 8/2000 |
| WO | WO00/58479 A1 | 10/2000 |
| WO | WO00/77030 A1 | 12/2000 |
| WO | WO 01/70672 | 9/2001 |

OTHER PUBLICATIONS

Abad–Zapatero,et al., "Structure of a secreted aspartic protease from *C. albicans* complexed with a potent inhibitor: implications for the design of antifungal agents," Protein Sci 5(4):640–52 (1996).

Abbenate, et al., "Inhibitors of –amyloid formation based on the –secretase cleavage site," *Biochemical and Biophysical Research Communications* 268(1):133–135 (2000).

Askew, et al., "Molecular recognition with convergent functional groups. Synthetic and structural studies with a model receptor for nucleic acid components," *J. Am. Chem. Soc.* 111, 1082–1090 (1989).

(List continued on next page.)

*Primary Examiner*—Michael Borin
*Assistant Examiner*—Shuba Zhou
(74) *Attorney, Agent, or Firm*—Hamilton, Brook, Smith & Reynolds, P.C.

(57) ABSTRACT

Methods for the production of purified, catalytically active, recombinant memapsin 2 have been developed. The substrate and subsite specificity of the catalytically active enzyme have been determined. The substrate and subsite specificity information was used to design substrate analogs of the natural memapsin 2 substrate that can inhibit the function of memapsin 2. The substrate analogs are based on peptide sequences, shown to be related to the natural peptide substrates for memapsin 2. The substrate analogs contain at least one analog of an amide bond which is not capable of being cleaved by memapsin 2. Processes for the synthesis of two substrate analogues including isosteres at the sites of the critical amino acid residues were developed and the substrate analogues, OMR99-1 and OM99-2, were synthesized. OM99-2 is based on an octapeptide Glu-Val-Asn-Leu-Ala-Ala-Glu-Phe (SEQ ID NO:28) with the Leu-Ala peptide bond substituted by a transition-state isostere hydroxyethylene group (FIG. 1). The inhibition constant of OM99-2 is $1.6 \times 10^{-9}$M against recombinant pro-memapsin 2. Crystallography of memapsin 2 bound to this inhibitor was used to determine the three dimensional structure of the protein, as well as the importance of the various residues in binding. This information can be used by those skilled in the art to design new inhibitors, using commercially available software programs and techniques familiar to those in organic chemistry and enzymology, to design new inhibitors to memapsin 2, useful in diagnostics and for the treatment and/or prevention of Alzheimer's disease.

18 Claims, 12 Drawing Sheets

OTHER PUBLICATIONS

Bailey & Cooper, "A structural comparison of 21 inhibitor complexes of the aspartic proteinase from *Endothia parasitica*," Protein Sci 3(11):2129–43 (1994).

Brunger, et al., "Crystallography & NMR system: A new software suite for macromolecular structure determination," Acta Crystallogr D Biol Crystallogr 54 ( Pt 5):905–21 (1998).

Capell, et al., "The proteolytic fragments of the Alzheimer's disease–associated presenilin–1 form heterodimers and occur as a 100–150–kDa molecular mass complex," J Biol Chem 273(6):3205–11 (1998).

Chartier–Harlin, et al., "Early–onset Alzheimer's disease caused by mutations at codon 717 of the beta–amyloid precursor protein gene," Nature 353(6347):844–6 (1991).

Citron, et al., "Mutation of the beta–amyloid precursor protein in familial Alzheimer's disease increases beta–protein production," Nature 360(6405):672–4 (1992).

Cohen, et al., "An artificial cell–cycle inhibitor isolated from a combinatorial library," Proc Natl Acad Sci U S A 95(24):14272–7 (1998).

Corder, et al., "Gene dose of apolipoprotein E type 4 allele and the risk of Alzheimer's disease in late onset families," Science 261(5123):921–3 (1993).

Cowley, et al., "Alzheimer's unlocking the mystery," *Newsweek* Jan. 31, 2000.

Cutfield, et al., "The crystal structure of a major secreted aspartic proteinase from *Candida albicans* in complexes with two inhibitors," Structure 3(11):1261–71 (1995).

Davies, "The structure and function of the aspartic proteinases," Annu Rev Biophys Chem 19:189–215 (1990).

De Strooper, et al., "Deficiency of presenilin–1 inhibits the normal cleavage of amyloid precursor protein," Nature 391(6665):387–90 (1998).

Dealwis, et al., "X–ray analysis at 2.0 A resolution of mouse submaxillary renin complexed with a decapeptide inhibitor CH–66, based on the 4–16 fragment of rat angiotensinogen," *J. Mol. Biol.* 236(1):342–60 (1994).

Dunn, Structure and Functions of the Aspartic Proteinases, Adv. in Exptl. Med. Biol. 306 (Plenum Press, NY 1991).

Ellington & Szostak, "In vitro selection of RNA molecules that bind specific ligands," Nature 346(6287):818–22 (1990).

Fan, et al., "BACE Maps to chromosome 11 and a BACE homolog, BACE2, reside in the obligate down syndrome region of chromosome 21," *Science* 286:1255a (1999).

Fields & Song, "A novel genetic system to detect protein––protein interactions," Nature 340(6230):245–6 (1989).

Ghosh & Fidanze, Transition–state mimetics for HIV protease inhibitors: Stereocontrolled synthesis of hydroxyethylene and hydroxyethylamine isosteres by ester–derived titanium enolate syn and anti–aldol reactions, *Org. Chem.* 63:6146–54 (1998).

Glenner & Wong, "Alzheimer's disease: initial report of the purification and characterization of a novel cerebrovascular amyloid protein," Biochem Biophys Res Commun 120(3):885–90 (1984).

Goate, et al., "Segregation of a missense mutation in the amyloid precursor protein gene with familial Alzheimer's disease," Nature 349(6311):704–6 (1991).

Goldgaber, et al., "Characterization and chromosomal localization of a cDNA encoding brain amyloid of Alzheimer's disease," Science 235(4791):877–80 (1987).

Haass & De Strooper, "The presenilins in Alzheimer's disease—Proteolysis holds the key," Science 286:916–919 (1999).

James, Aspartic Proteinases, Retroviral and Cellular Enzymes, Adv. in Exptl. Med. Biol. 436 (Plenum Press, NY 1998).

Jones, et al., "Improved methods for binding protein models in electron density maps and the location of errors in these models" Acta Crystallogr A 47 ( Pt 2):110–9 (1991).

Jorm, ed., *A Guide to the Understanding of Alzheimer's Disease and Related Disorders* (New York University Press, New York 1987).

Kang, et al., "The precursor of Alzheimer's disease amyloid A4 protein resembles a cell–surface receptor," Nature 325(6106):733–6 (1987).

Kearney & Aweeka, "The penetration of anti–infectives into the central nervous system," *Neurol. Clin.* 17(4):883–900 (1999).

Kelly & Dow, "Microbial differentiation: the role of cellular asymmetry," *Microbiol Sci* 1(9):214–9 (1984).

Khan, et al., "Lowering the entropic barrier for binding conformationally flexible inhibitors to enzymes," Biochemistry 37(48):16839–45 (1998).

Knops, et al., "Cell–type and amyloid precursor protein–type specific inhibition of A beta release by bafilomycin A1, a selective inhibitor of vacuolar ATPases," J Biol Chem 270(6):2419–22 (1995).

Kolata, "Scientists find enzyme linked to Alzheimer's," National Science/Health Oct. 22, 1999.

Kostka, *Aspartic proteinases and Their Inhibitor* (Walter de Gruyter, Berlin 1985).

Laskowski, et al., "Procheck: a program to check the stereochemical quality of protein structures," *J Appl. Crystallog* 26:283 (1993).

Lemaire, et al., "The PreA4(695) precursor protein of Alzheimer's disease A4 amyloid is encoded by 16 exons," Nucleic Acids Res 17(2):517–22 (1989).

Levy ,et al., "Mutation of the Alzheimer's disease amyloid gene in hereditary cerebral hemorrhage, Dutch type," Science 248(4959):1124–6 (1990).

Levy–Lahad, et al., "Candidate gene for the chromosome 1 familial Alzheimer's disease locus," Science 269(5226):973–7 (1995).

Lewis & Dean, "Automated site–directed drug design: the concept of spacer skeletons for primary structure generation," Proc R Soc Lond B Biol Sci 236(1283):125–40 and 141–162 (1989).

Lin, et al., "Intracellular diversion of glycoprotein GP160 of human immunodeficiency virus to lysosomes as a strategy of AIDS gene therapy," *FASEB J* 7(11):1070–80 (1993).

Mann, "Cerebral amyloidosis, ageing and Alzheimer's disease; a contribution from studies on Down's syndrome," Neurobiol Aging 10(5):397–9 (1989).

Marciniszyn, et al., "Mode of inhibition of acid proteases by pepstatin," *J. Biol. Chem.* 251(22):7088–94 (1976).

Matsumoto, et al., "Molecular cloning of human cDNA with a sequence highly similar to that of the dihydrofolate reductase gene in brain libraries derived from Alzheimer's disease patients," *Eur. J. Biochem.* 230:337–343 (1995).

McKinlay & Rossmann, "Rational design of antiviral agents," Annu Rev Pharmacol Toxicol 29:111–22 (1989).

Meckelein, et al., "Identification of a novel serine protease–like molecule in human brain," *Molecular Brain Research* 55:181–197 (1998).

Mullan, et al., "A locus for familial early–onset Alzheimer's disease on the long arm of chromosome 14, proximal to the alpha 1–antichymotrypsin gene," Nat Genet 2(4):340–2 (1992).

Mullan, et al., "A pathogenic mutation for probable Alzheimer's disease in the APP gene at the N–terminus of beta–amyloid," Nat Genet 1(5):345–7 (1992).

Murrell, et al., "A mutation in the amyloid precursor protein associated with hereditary Alzheimer's disease," Science 254(5028):97–9 (1991).

Navada, "AMoRe: an automated package for molecualr replacement," *Acta Crystallog Sect A* 50:157 (1997).

Otwinowski & Minor, "Processing of X–ray diffraction data collected in Oscillation mode," *Methods Enzymol* 276:307 (1997).

Perez, et al., "Enhanced release of amyloid beta–protein from codon 670/671 "Swedish" mutant beta–amyloid precursor protein occurs in both secretory and endocytic pathways, " J Biol Chem 271(15):9100–7 (1996).

Perry & Davies, *QSAR: Quantitative Structure–Activity Relationships in Drug Design* pp. 189–193 (Alan R. Liss, Inc. 1989).

Phimister, "Four companies announce discovery of b–secretase gene," *Nature Biotechnology* 18:16 (2000).

Podlisny, et al., "Presenilin proteins undergo heterogeneous endoproteolysis between Thr291 and Ala299 and occur as stable N– and C–terminal fragments in normal and Alzheimer brain tissue," Neurobiol Dis 3(4):325–37 (1997).

Ripka, "Computers picture the perfect drug," *New Scientist* 54–57 (1988).

Robakis, et al., "Molecular cloning and characterization of a cDNA encoding the cerebrovascular and the neuritic plaque amyloid peptides," Proc Natl Acad Sci U S A 84(12):4190–4 (1987).

Roberts & Szostak, "RNA–peptide fusions for the in vitro selection of peptides and proteins," Proc Natl Acad Sci U S A 94(23):12297–302 (1997).

Rogaev, et al., "Familial Alzheimer's disease in kindreds with missense mutations in a gene on chromosome 1 related to the Alzheimer's disease type 3 gene," Nature 376(6543):775–8 (1995).

Rouvinen, et al., "Computer aided drug design," *Acta Pharmaceutica Fennica* 97, 159–166 (1988).

Rumble, et al., "Amyloid A4 protein and its precursor in Down's syndrome and Alzheimer's disease," *N Engl J Med* 320(22):1446–52 (1989).

pg,9

Selkoe, et al., "Translating cell biology into therapeutic advances in Alzheimer's diseae," Nature 399(6738 Suppl):A23–31 (1999).

Sherrington, et al., "Cloning of a gene bearing missense mutations in early–onset familial Alzheimer's disease," Nature 375(6534):754–60 (1995).

Sinha & Lieberburg, "Cellular mechanisms of beta–amyloid production and secretion," Proc Natl Acad Sci U S A 96(20):11049–53 (1999).

Sinha, et al., "Purification and cloning of amyloid precursor protein beta–secretase from human brain," Nature 402(6761):537–40 (1999).

Steiner, et al., "Expression of Alzheimer's disease–associated presenilin–1 is controlled by proteolytic degradation and complex formation," J Biol Chem 273(48):32322–31 (1998).

Suzuki, et al., "An increased percentage of long amyloid beta protein secreted by familial amyloid beta protein precursor (beta APP717) mutants," Science 264(5163):1336–40 (1994).

Symersky, et al., "High–resolution structure of the extracellular aspartic proteinase from *Candida tropicalis* yeast," Biochemistry 36(42):12700–10 (1997).

Szostak, "In vitro genetics," *TIBS* 19:89, (1992).

Tagawa, et al., "Alzheimer's disease amyloid –clipping enzyme (APP secretase): Identification, purification, and characterization of the enzyme," *Biochemical and Biophysical Research Communications* 177(1):377–387 (1991).

Takahashi, Aspartic Proteases, Structure, Function, Biology, Biomedical Implications, Adv. in Exptl. Med. Biol. 362 (Plenum Press, NY 1995).

Tang, Acid Proteases, Structure, Function and Biology, Adv. in Exptl. Med. Biol. vol. 95 (Plenum Press, NY 1977).

Tang, et al., "Structural evidence for gene duplication in the evolution of the acid proteases," Nature 271(5646):618–21 (1978).

Tanzi, et al., "Protease inhibitor domain encoded by an amyloid protein precursor mRNA associated with Alzheimer's disease," Nature 331(6156):528–30 (1988).

*The early story of Alzheimer's Disease*, edited by Bick et al. (Raven Press, New York 1987).

Thinakaran, et al., "Endoproteolysis of presenilin 1 and accumulation of processed derivatives in vivo," Neuron 17(1):181–90 (1996).

Thinakaran, et al., "Evidence that levels of presenilins (PS1 and PS2) are coordinately regulated by competition for limiting cellular factors," J Biol Chem 272(45):28415–22 (1997).

Thinakaran, et al., "Stable association of presenilin derivatives and absence of presenilin interactions with APP," Neurobiol Dis 4(6):438–53 (1998).

Van Broeckhoven, et al.,"Amyloid beta protein precursor gene and hereditary cerebral hemorrhage with amyloidosis (Dutch)," Science 248(4959):1120–2 (1990).

Vassar, et al.,"Beta–secretase cleavage of Alzheimer's amyloid precursor protein by the transmembrane aspartic protease BACE," Science 286(5440):735–41 (1999).

Wolfe, et al., "Two transmembrane aspartates in presenilin–1 required for presenilin endoproteolysis and gamma–secretase activity," Nature 398(6727):513–7 (1999).

Yang & Quail, "Structure of the Rhizomucor miehei aspartic proteinase complexed with the inhibitor pepstatin A at 2.7 A resolution," Acta Crystallogr D Biol Crystallogr 55 ( Pt 3):625–30 (1999).

Yoshikai, et al., "Genomic organization of the human amyloid beta–protein precursor gene," Gene 87(2):257–63 (1990).

Yu, "Inhibition of beta–amyloid cytotoxicity by midkine," *Neurosci Lett* 254(3):125–8 (1998).

Ermolieff, et al., "Proteolytic activation of recombinant Pro–memapsin 2 (Pro– –secretase) studied with new flourogenic substrtes," *Biochemistry* 39(40):12450–12456 (2000).

Ghosh, et al., "Design of potent inhibitors for human brain memapsin 2 ( –sevretase)," *J Am Chem Soc* 122(14):3522–3523 (2000).

Hong, et al., "Structure of the protease domain of memapsin 2 ( –secretase) complexed with inhibitor," *Science* 290:150–153 (2000).

Lin, et al., "Human aspartic protease memapsin 2 cleaves the –secretase site of –amyloid precursor protein," *PNAS* 97(4):1456–1460 (2000).

Turner, et al., "Substrate specify of memapsin 2 ( –secretase): basis for inhibitor drug design for Alzeimer's disease," Experimental Biology 2001 c/o *FASEB* Office of Scientific Meetings Mar. 31–Apr. 4, 2001, Orlando, Florida. (Abstract).

Ezzell, C., "Alzheimer's Alchemy," *Science News* 141:152–153 (1992).

Paris, N., et al., "Bacterial Production and Purification of Recombinant Human Prolactin," *Biotech and App Biochem* 12: 436–449 (1990).

Varon, S., et al., "Neuronotrophic and Neurite–Promoting Factors and Their Clinical Potentials," *Dev. Neurosci*, 6: 73–100 (1983–84).

Gurney, M.E. et al., U.S. Published Patent application, US 2002/0081634 A1, published Jun. 27, 2002, filing date Apr. 5, 2001.

JP10108681A, Adams, M.D., et al., Cathepsin K Gene Abstract. MicroPatent Bibliographic Database [Online]. [Retrieved on 1999–11–30].Retrieved from the Internet <URL:http://www.micropat.com/htdocs/com.../nerac.00587727/JP/JP10108681.html>.

Hook, V.Y.H., U.S. Published Patent application, US 2002/0072050 A1, published Jun. 13, 2002, filing date Feb. 28, 2001.

Chopra, R. et al., U.S. Published Patent application, US 2002/0055459 A1, published May 9, 2002, filing date Sep. 19, 2001.

\* cited by examiner

FIG. 1

```
1v   MASMTGGQQM GRGSMAGVLP AHGTQHGIRL PLRSGLGGAP LGLRLPRETD
36p  EEPEEPGRRG SFVEMVDNLR GKSGQGYYVE MTVGSPPQTL NILVDTGSSN
38   FAVGAAPHPF LHRYYQRQLS STYRDLRKGV YVPYTQGKWE GELGTDLVSI
88   PHGPNVTVRA NIAAITESDK FFINGSNWEG ILGLAYAEIA RPDDSLEPFF
138  DSLVKQTHVP NLFSLQLCGA GFPLNQSEVL ASVGGSMIIG GIDHSLYTGS
188  LWYTPIRREW YYEVIIVRVE INGQDLKMDC KEYNYDKSIV DSGTTNLRLP
238  KKVFEAAVKS IKAASSTEKF PDGFWLGEQL VCWQAGTTPW NIFPVISLYL
288  MGEVTNQSFR ITILPQQYLR PVEDVATSQD DCYKFAISQS STGTVMGAVI
338  MEGFYVVFDR ARKRIGFAVS ACHVHDEFRT AAVEGPFVTL DMEDCGYNIP
388  QTDEST LMTI AYVMAAICAL FMLPLCLMVC QWRCLRCLRQ QHDDFADDIS
     T1→
438  LLK*
```

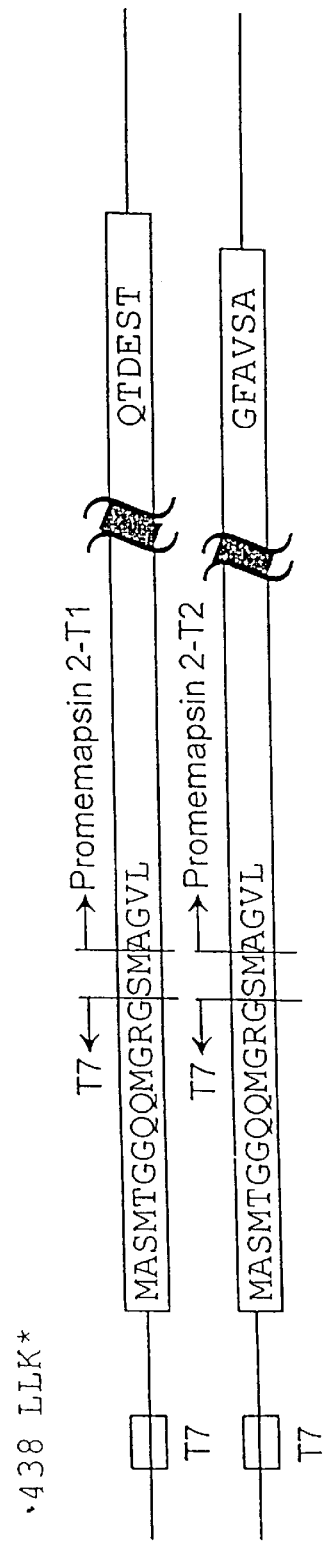

OM99-1

OM99-2

[Mep2] = 0.47 µM
[Fluo. Substrate] = 29.9 µM
Buffer: Na Acetate 0.1 M, 5% DMSO, pH 4.5 at 37°C
Excitation at 350 nm
Emission at 490 nm

| Parameter | Value | Std. Error |
|---|---|---|
| Ki | 6.84 e - 8 | 2.72 e - 9 |

$[E]_o = 0.11 \mu M$
$[Fluo\ Substrate] = 29.9\ \mu M$

| Parameter | Value | Std. Error |
|---|---|---|
| Ki | 9.58e-9 | 2.86e-10 |

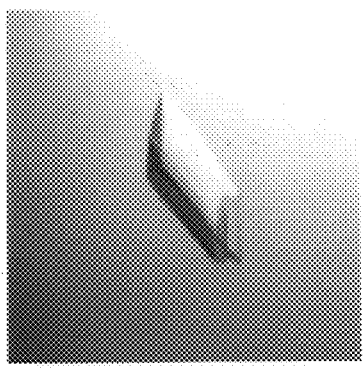
FIG. 5A
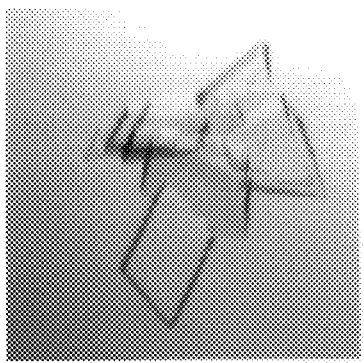
FIG. 5B
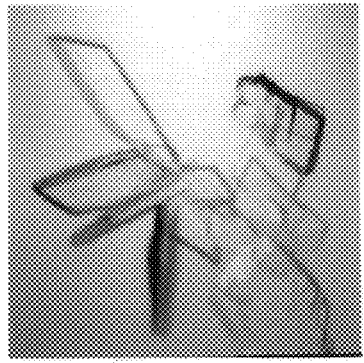
FIG. 5C
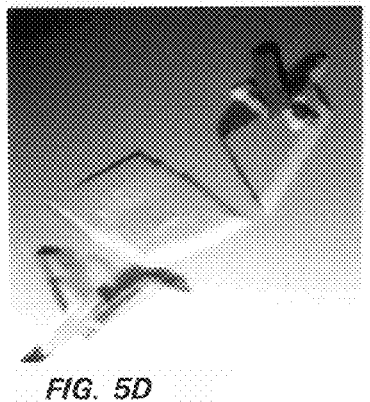
FIG. 5D
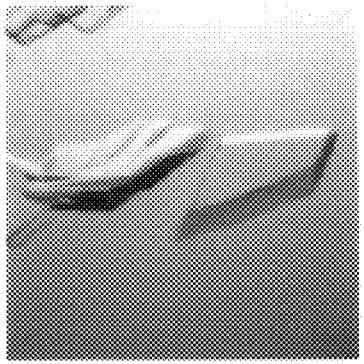
FIG. 5E
FIG. 5

SEQUENCE LISTING

```
<160> NUMBER OF SEQ ID NOS:  31

<210> SEQ ID NO 1
<211> LENGTH: 3252
<212> TYPE: DNA
<213> ORGANISM: Homo sapiens

<400> SEQUENCE: 1
gcgggagtgc tgcctgccca cggcacccag cacggcatcc ggctgcccct gcgcagcggc        60 ctgggggcg ccccctggg gctgcggctg ccccgggaga ccgacgaaga gcccgaggag         120
cccggccgga ggggcagctt tgtggagatg gtggacaacc tgagggcaa gtcggggcag        180 ggctactacg tggagatgac cgtgggcagc ccccgcaga cgctcaacat cctggtggat        240
acaggcagca gtaactttgc agtgggtgct gcccccacc ccttcctgca tcgctactac        300
cagaggcagc tgtccagcac ataccgggac ctccggaagg gtgtgtatgt gccctacacc       360
cagggcaagt gggaagggga gctgggcacc gacctggtaa gcatccccca tggccccaac       420
gtcactgtgc gtgccaacat tgctgccatc actgaatcag acaagttctt catcaacggc       480
tccaactggg aaggcatcct ggggctggcc tatgctgaga ttgccaggcc tgacgactcc       540
ctggagcctt tctttgactc tctggtaaag cagacccacg ttcccaacct cttctccctg       600
cagctttgtg gtgctggctt cccctcaac cagtctgaag tgctggcctc tgtcggaggg       660
agcatgatca ttggaggtat cgaccactcg ctgtacacag gcagtctctg gtatacaccc       720
atccggcggg agtggtatta tgaggtgatc attgtgcggg tggagatcaa tggacaggat       780
ctgaaaatgg actgcaagga gtacaactat gacaagagca ttgtggacag tggcaccacc       840
```

```
aaccttcgtt tgcccaagaa agtgtttgaa gctgcagtca aatccatcaa ggcagcctcc    900
tccacggaga agttccctga tggtttctgg ctaggagagc agctggtgtg ctggcaagca    960
ggcaccaccc cttggaacat tttcccagtc atctcactct acctaatggg tgaggttacc   1020
aaccagtcct tccgcatcac catccttccg cagcaatacc tgcggccagt ggaagatgtg   1080
gccacgtccc aagacgactg ttacaagttt gccatctcac agtcatccac gggcactgtt   1140
atgggagctg ttatcatgga gggcttctac gttgtctttg atcgggcccg aaaacgaatt   1200
ggctttgctg tcagcgcttg ccatgtgcac gatgagttca ggacgcagc ggtggaaggc    1260
ccttttgtca ccttggacat ggaagactgt ggctacaaca ttccacagac agatgagtca   1320
accctcatga ccatagccta tgtcatggct gccatctgcg ccctcttcat gctgccactc   1380
tgcctcatgg tgtgtcagtg gcgctgcctc cgctgcctgc ccagcagca tgatgacttt    1440
gctgatgaca tctccctgct gaagtgagga ggcccatggg cagaagatag agattcccct   1500
ggaccacacc tccgtggttc actttggtca caagtaggag acacagatgg cacctgtggc   1560
cagagcacct caggaccctc cccacccacc aaatgcctct gccttgatgg agaaggaaaa   1620
ggctggcaag gtgggttcca gggactgtac ctgtaggaaa cagaaaagag aagaaagaag   1680
cactctgctg gcgggaatac tcttggtcac ctcaaattta agtcgggaaa ttctgctgct   1740
tgaaacttca gccctgaacc tttgtccacc attcctttaa attctccaac ccaaagtatt   1800
cttcttttct tagtttcaga agtactggca tcacacgcag gttaccttgg cgtgtgtccc   1860
tgtggtaccc tggcagagaa gagaccaagc ttgtttccct gctggccaaa gtcagtagga   1920
gaggatgcac agtttgctat ttgctttaga gacagggact gtataaacaa gcctaacatt   1980
ggtgcaaaga ttgcctcttg aattaaaaaa aaactagatt gactatttat acaaatgggg   2040
gcggctggaa agaggagaag gagagggagt acaaagacag ggaatagtgg gatcaaagct   2100
aggaaaggca gaaacacaac cactcaccag tcctagtttt agacctcatc tccaagatag   2160
catcccatct cagaagatgg gtgttgtttt caatgttttc ttttctgtgg ttgcagcctg   2220
accaaaagtg agatgggaag ggcttatcta gccaaagagc tcttttttag ctctcttaaa   2280
tgaagtgccc actaagaagt tccacttaac acatgaattt ctgccatatt aatttcattg   2340
tctctatctg aaccacccct tattctacat atgataggca gcactgaaat atcctaaccc   2400
cctaagctcc aggtgccctg tgggagagca actggactat agcagggctg gctctgtct    2460
tcctggtcat aggctcactc tttccccaa atcttcctct ggagctttgc agccaaggtg    2520
ctaaaaggaa taggtaggag acctcttcta tctaatcctt aaaagcataa tgttgaacat   2580
tcattcaaca gctgatgccc tataaccct gcctggattt cttcctatta ggctataaga    2640
agtagcaaga tctttacata attcagagtg gtttcattgc cttcctaccc tctctaatgg   2700
cccctccatt tatttgacta aagcatcrca cagtggcact agcattatac caagagtatg   2760
agaaatacag tgctttatgg ctctaacatt actgccttca gtatcaaggc tgcctggaga   2820
aaggatggca gcctcaggc ttccttatgt cctccaccac aagagctcct tgatgaaggt    2880
catctttttc ccctatcctg ttcttcccct cccgctcct aatggtacgt gggtacccag    2940
gctggttctt gggctaggta gtggggacca agttcattac ctccctatca gttctagcat   3000
agtaaactac ggtaccagtg ttagtgggaa gagctgggtt ttcctagtat acccactgca   3060
tcctactcct acctggtcaa cccgctgctt ccaggtatgg gacctgctaa gtgtggaatt   3120
acctgataag ggagagggaa atacaaggag ggcctctggt gttcctggcc tcagccagct   3180
```

```
gcccmcaagc cataaaccaa taaamcaaga atactgagtc taaaaaaaaa aaaaaaaaaa   3240
aaaaaaaaaa aa                                                       3252
```

<210> SEQ ID NO 2
<211> LENGTH: 488
<212> TYPE: PRT
<213> ORGANISM: Homo sapiens
<220> FEATURE:
<223> OTHER INFORMATION: Purified Memapsin 2
<223> OTHER INFORMATION: Amino Acids 28-48 are remnant putative
      propeptide residues
<223> OTHER INFORMATION: Amino Acids 58-61, 78, 80, 82-83, 116, 118-121,
      156, 166, 174, 246, 274, 276, 278-281, 283, and
      376-377 are residues in contact with the OM99-2
      inhibitor
<223> OTHER INFORMATION: Amino acids 54-57, 61-68, 73-80, 86-89,
      109-111, 113-118, 123-134, 143-154, 165-168, 198-202, and 220-224
      are N-lobe Beta Strands
<223> OTHER INFORMATION: Amino Acids 184-191 and 210-217 are N-lobe
      Helices
<223> OTHER INFORMATION: Amino acids 237-240, 247-249, 251-256, 259-260,
      273-275, 282-285, 316-318, 331-336, 342-348,
      354-357, 366-370, 372-375, 380-383, 390-395,
      400-405, and 418-420 are C-lobe Beta Strands
<223> OTHER INFORMATION: Amino Acids 286-299, 307-310, 350-353, 384-387,
      and 427-431 are C-lobe Helices

<400> SEQUENCE: 2

```
Ala Gly Val Leu Pro Ala His Gly Thr Gln His Gly Ile Arg Leu Pro
1               5                   10                  15

Leu Arg Ser Gly Leu Gly Gly Ala Pro Leu Gly Leu Arg Leu Pro Arg
            20                  25                  30

Glu Thr Asp Glu Glu Pro Glu Glu Pro Gly Arg Arg Gly Ser Phe Val
        35                  40                  45

Glu Met Val Asp Asn Leu Arg Gly Lys Ser Gly Gln Gly Tyr Tyr Val
    50                  55                  60

Glu Met Thr Val Gly Ser Pro Pro Gln Thr Leu Asn Ile Leu Val Asp
65                  70                  75                  80

Thr Gly Ser Ser Asn Phe Ala Val Gly Ala Ala Pro His Pro Phe Leu
                85                  90                  95

His Arg Tyr Tyr Gln Arg Gln Leu Ser Ser Thr Tyr Arg Asp Leu Arg
            100                 105                 110

Lys Gly Val Tyr Val Pro Tyr Thr Gln Gly Lys Trp Glu Gly Glu Leu
        115                 120                 125

Gly Thr Asp Leu Val Ser Ile Pro His Gly Pro Asn Val Thr Val Arg
    130                 135                 140

Ala Asn Ile Ala Ala Ile Thr Glu Ser Asp Lys Phe Phe Ile Asn Gly
145                 150                 155                 160

Ser Asn Trp Glu Gly Ile Leu Gly Leu Ala Tyr Ala Glu Ile Ala Arg
                165                 170                 175

Pro Asp Asp Ser Leu Glu Pro Phe Phe Asp Ser Leu Val Lys Gln Thr
            180                 185                 190

His Val Pro Asn Leu Phe Ser Leu Gln Leu Cys Gly Ala Gly Phe Pro
        195                 200                 205

Leu Asn Gln Ser Glu Val Leu Ala Ser Val Gly Gly Ser Met Ile Ile
    210                 215                 220

Gly Gly Ile Asp His Ser Leu Tyr Thr Gly Ser Leu Trp Tyr Thr Pro
225                 230                 235                 240

Ile Arg Arg Glu Trp Tyr Tyr Glu Val Ile Ile Val Arg Val Glu Ile
                245                 250                 255
```

-continued

Asn Gly Gln Asp Leu Lys Met Asp Cys Lys Glu Tyr Asn Tyr Asp Lys
            260                 265                 270

Ser Ile Val Asp Ser Gly Thr Thr Asn Leu Arg Leu Pro Lys Lys Val
        275                 280                 285

Phe Glu Ala Ala Val Lys Ser Ile Lys Ala Ala Ser Ser Thr Glu Lys
    290                 295                 300

Phe Pro Asp Gly Phe Trp Leu Gly Glu Gln Leu Val Cys Trp Gln Ala
305                 310                 315                 320

Gly Thr Thr Pro Trp Asn Ile Phe Pro Val Ile Ser Leu Tyr Leu Met
                325                 330                 335

Gly Glu Val Thr Asn Gln Ser Phe Arg Ile Thr Ile Leu Pro Gln Gln
            340                 345                 350

Tyr Leu Arg Pro Val Glu Asp Val Ala Thr Ser Gln Asp Asp Cys Tyr
        355                 360                 365

Lys Phe Ala Ile Ser Gln Ser Ser Thr Gly Thr Val Met Gly Ala Val
    370                 375                 380

Ile Met Glu Gly Phe Tyr Val Val Phe Asp Arg Ala Arg Lys Arg Ile
385                 390                 395                 400

Gly Phe Ala Val Ser Ala Cys His Val His Asp Glu Phe Arg Thr Ala
                405                 410                 415

Ala Val Glu Gly Pro Phe Val Thr Leu Asp Met Glu Asp Cys Gly Tyr
            420                 425                 430

Asn Ile Pro Gln Thr Asp Glu Ser Thr Leu Met Thr Ile Ala Tyr Val
        435                 440                 445

Met Ala Ala Ile Cys Ala Leu Phe Met Leu Pro Leu Cys Leu Met Val
    450                 455                 460

Cys Gln Trp Arg Cys Leu Arg Cys Leu Arg Gln Gln His Asp Asp Phe
465                 470                 475                 480

Ala Asp Asp Ile Ser Leu Leu Lys
                485

<210> SEQ ID NO 3
<211> LENGTH: 503
<212> TYPE: PRT
<213> ORGANISM: Homo sapiens
<220> FEATURE:
<223> OTHER INFORMATION: Pro-memapsin 2
<223> OTHER INFORMATION: Amino Acids 1-15 are vector-derived residues
<223> OTHER INFORMATION: Amino Acids 16-64 are a putative pro peptide
<223> OTHER INFORMATION: Amino Acids 1-13 are the T7 promoter
<223> OTHER INFORMATION: Amino Acids 16-456 are Pro-memapsin 2-T1
<223> OTHER INFORMATION: Amino Acids 16-421 are Promemapsin 2-T2

<400> SEQUENCE: 3

Met Ala Ser Met Thr Gly Gly Gln Gln Met Gly Arg Gly Ser Met Ala
1               5                   10                  15

Gly Val Leu Pro Ala His Gly Thr Gln His Gly Ile Arg Leu Pro Leu
            20                  25                  30

Arg Ser Gly Leu Gly Gly Ala Pro Leu Gly Leu Arg Leu Pro Arg Glu
        35                  40                  45

Thr Asp Glu Glu Pro Glu Glu Pro Gly Arg Arg Gly Ser Phe Val Glu
    50                  55                  60

Met Val Asp Asn Leu Arg Gly Lys Ser Gly Gln Gly Tyr Tyr Val Glu
65                  70                  75                  80

Met Thr Val Gly Ser Pro Pro Gln Thr Leu Asn Ile Leu Val Asp Thr
                85                  90                  95

Gly Ser Ser Asn Phe Ala Val Gly Ala Ala Pro His Pro Phe Leu His

```
                100              105              110
Arg Tyr Tyr Gln Arg Gln Leu Ser Ser Thr Tyr Arg Asp Leu Arg Lys
            115              120              125
Gly Val Tyr Val Pro Tyr Thr Gln Gly Lys Trp Glu Gly Glu Leu Gly
130              135              140
Thr Asp Leu Val Ser Ile Pro His Gly Pro Asn Val Thr Val Arg Ala
145              150              155              160
Asn Ile Ala Ala Ile Thr Glu Ser Asp Lys Phe Phe Ile Asn Gly Ser
            165              170              175
Asn Trp Glu Gly Ile Leu Gly Leu Ala Tyr Ala Glu Ile Ala Arg Pro
            180              185              190
Asp Asp Ser Leu Glu Pro Phe Phe Asp Ser Leu Val Lys Gln Thr His
            195              200              205
Val Pro Asn Leu Phe Ser Leu Gln Leu Cys Gly Ala Gly Phe Pro Leu
            210              215              220
Asn Gln Ser Glu Val Leu Ala Ser Val Gly Gly Ser Met Ile Ile Gly
225              230              235              240
Gly Ile Asp His Ser Leu Tyr Thr Gly Ser Leu Trp Tyr Thr Pro Ile
            245              250              255
Arg Arg Glu Trp Tyr Tyr Glu Val Ile Ile Val Arg Val Glu Ile Asn
            260              265              270
Gly Gln Asp Leu Lys Met Asp Cys Lys Glu Tyr Asn Tyr Asp Lys Ser
            275              280              285
Ile Val Asp Ser Gly Thr Thr Asn Leu Arg Leu Pro Lys Lys Val Phe
            290              295              300
Glu Ala Ala Val Lys Ser Ile Lys Ala Ala Ser Ser Thr Glu Lys Phe
305              310              315              320
Pro Asp Gly Phe Trp Leu Gly Glu Gln Leu Val Cys Trp Gln Ala Gly
            325              330              335
Thr Thr Pro Trp Asn Ile Phe Pro Val Ile Ser Leu Tyr Leu Met Gly
            340              345              350
Glu Val Thr Asn Gln Ser Phe Arg Ile Thr Ile Leu Pro Gln Gln Tyr
            355              360              365
Leu Arg Pro Val Glu Asp Val Ala Thr Ser Gln Asp Asp Cys Tyr Lys
370              375              380
Phe Ala Ile Ser Gln Ser Ser Thr Gly Thr Val Met Gly Ala Val Ile
385              390              395              400
Met Glu Gly Phe Tyr Val Val Phe Asp Arg Ala Arg Lys Arg Ile Gly
            405              410              415
Phe Ala Val Ser Ala Cys His Val His Asp Glu Phe Arg Thr Ala Ala
            420              425              430
Val Glu Gly Pro Phe Val Thr Leu Asp Met Glu Asp Cys Gly Tyr Asn
            435              440              445
Ile Pro Gln Thr Asp Glu Ser Thr Leu Met Thr Ile Ala Tyr Val Met
450              455              460
Ala Ala Ile Cys Ala Leu Phe Met Leu Pro Leu Cys Leu Met Val Cys
465              470              475              480
Gln Trp Arg Cys Leu Arg Cys Leu Arg Gln Gln His Asp Asp Phe Ala
            485              490              495
Asp Asp Ile Ser Leu Leu Lys
            500

<210> SEQ ID NO 4
```

```
<211> LENGTH: 10
<212> TYPE: PRT
<213> ORGANISM: Artificial Sequence
<220> FEATURE:
<223> OTHER INFORMATION: Description of Artificial Sequence: Primer

<400> SEQUENCE: 4

Ser Glu Val Lys Met Asp Ala Glu Phe Arg
 1               5                  10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 5

Ser Glu Val Asn Leu Asp Ala Glu Phe Arg
 1               5                  10

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 6

Ser Val Asn Met Ala Glu Gly Asp
 1               5

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 7

Lys Gly Gly Val Val Ile Ala Thr Val Ile Val Lys
 1               5                  10

<210> SEQ ID NO 8
<211> LENGTH: 4
<212> TYPE: PRT
<213> ORGANISM: Homo sapiens

<400> SEQUENCE: 8

Asp Thr Ser Gly
 1

<210> SEQ ID NO 9
<211> LENGTH: 8
<212> TYPE: PRT
<213> ORGANISM: Homo sapiens

<400> SEQUENCE: 9

Leu Val Asn Met Ala Glu Gly Asp
 1               5

<210> SEQ ID NO 10
<211> LENGTH: 28
<212> TYPE: DNA
```

<213> ORGANISM: Artificial Sequence
<220> FEATURE:
<223> OTHER INFORMATION: Description of Artificial Sequence: Primer

<400> SEQUENCE: 10
ggtaagcatc ccccatggcc ccaacgtc                28

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 11
gacgttgggg ccatggggga tgcttacc                28

<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 12
acgttgtctt tgatcgggcc cgaaaacgaa ttgg                34

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 13
ccaattcgtt ttcgggcccg atcaaagaca acg                33

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 14
ccatcctaat acgactcact atagggc                27

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 15
actcactata gggctcgagc ggc                23

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 16
cttttgagca agttcagcct ggttaa                26

```
<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 17
gaggtggctt atgagtattt cttccagggt a                            31

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 18
tggcgacgac tcctggagcc cg                                      22

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 19
tgacaccaga ccaactggta atgg                                    24

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 20
catatggcgg gagtgctgcc tgcccac                                 27

<210> SEQ ID NO 21
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 21
ggatcctcac ttcagcaggg agatgtcatc agcaaagt                     38

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Oxidized
      Insulin B-chain
<223> OTHER INFORMATION: Xaa at site 3 represents cysteic acid

<400> SEQUENCE: 22

His Leu Xaa Gly Ser His Leu Val
 1               5

<210> SEQ ID NO 23
<211> LENGTH: 8
```

```
<212> TYPE: PRT
<213> ORGANISM: Artificial Sequence
<220> FEATURE:
<223> OTHER INFORMATION: Description of Artificial Sequence: Oxidized
      Insulin B-chain
<223> OTHER INFORMATION: Xaa at site 1 represents cysteic acid

<400> SEQUENCE: 23

Xaa Gly Glu Arg Gly Phe Phe Tyr
  1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 24

Val Gly Ser Gly Val
  1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 25

Val Gly Ser Gly Val Leu Leu
  1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 26

Gly Val Leu Leu Ser Arg Lys
  1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Inhibitors

<400> SEQUENCE: 27

Val Asn Leu Ala Ala Glu Phe
  1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Inhibitors

<400> SEQUENCE: 28

Glu Val Asn Leu Ala Ala Glu Phe
  1               5
```

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 29

Asn Leu Ala Ala
  1

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 30

Val Gly Ser Gly Val Leu Leu Ser Arg Lys
  1               5                  10

<210> SEQ ID NO 31
<211> LENGTH: 326
<212> TYPE: PRT
<213> ORGANISM: Homo sapiens
<220> FEATURE:
<223> OTHER INFORMATION: Amino acids 2-5, 6-9, 13-20, 25-32, 65-67,
      69-74, 79-87, 89-91, 99-106, 119-122, 150-154, 164-167, 180-183,
      191-194, 196-199, 201-204, 210-214, 221-223, 258-262, 265-269, and
      275-278 are Beta
<223> OTHER INFORMATION: Amino acids 281-284, 286-288, 298-301, 310-315,
      and 319-324 are Beta strands
<223> OTHER INFORMATION: Amino acids 48-51, 111-114, 136-142, 225-234,
      249-254, 271-274, and 303-306 are Helices
<223> OTHER INFORMATION: Amino acids 12-13, 30, 32, 34-35, 73-77, 111,
      117, 120, 189, 213, 215, 217-220, 287, 289, 291, 298, and 300 are
      residues in contact with pepstatin.
<223> OTHER INFORMATION: Pepsin

<400> SEQUENCE: 31

Val Asp Glu Gln Pro Leu Glu Asn Tyr Leu Asp Met Glu Tyr Phe Gly
  1               5                  10                  15

Thr Ile Gly Ile Gly Thr Pro Ala Gln Asp Phe Thr Val Val Phe Asp
                 20                  25                  30

Thr Gly Ser Ser Asn Leu Trp Val Pro Ser Val Tyr Cys Ser Ser Leu
            35                  40                  45

Ala Cys Thr Asn His Asn Arg Phe Asn Pro Glu Asp Ser Ser Thr Tyr
        50                  55                  60

Gln Ser Thr Ser Glu Thr Val Ser Ile Thr Tyr Gly Thr Gly Ser Met
 65                  70                  75                  80

Thr Gly Ile Leu Gly Tyr Asp Thr Val Gln Val Gly Gly Ile Ser Asp
                 85                  90                  95

Thr Asn Gln Ile Phe Gly Leu Ser Glu Thr Glu Pro Gly Ser Phe Leu
            100                 105                 110

Tyr Tyr Ala Pro Phe Asp Gly Ile Leu Gly Leu Ala Tyr Pro Ser Ile
        115                 120                 125

Ser Ser Ser Gly Ala Thr Pro Val Phe Asp Asn Ile Trp Asn Gln Gly
    130                 135                 140

Leu Val Ser Gln Asp Leu Phe Ser Val Tyr Leu Ser Ala Asp Asp Gln
145                 150                 155                 160

-continued

```
Ser Gly Ser Val Val Ile Phe Gly Gly Ile Asp Ser Ser Tyr Tyr Thr
            165                 170                 175
Gly Ser Leu Asn Trp Val Pro Val Thr Val Glu Gly Tyr Trp Gln Ile
            180                 185                 190
Thr Val Asp Ser Ile Thr Met Asn Gly Glu Ala Ile Ala Cys Ala Glu
            195                 200                 205
Gly Cys Gln Ala Ile Val Asp Thr Gly Thr Ser Leu Leu Thr Gly Pro
    210                 215                 220
Thr Ser Pro Ile Ala Asn Ile Gln Ser Asp Ile Gly Ala Ser Glu Asn
225                 230                 235                 240
Ser Asp Gly Asp Met Val Val Ser Cys Ser Ala Ile Ser Ser Leu Pro
            245                 250                 255
Asp Ile Val Phe Thr Ile Asn Gly Val Gln Tyr Pro Val Pro Pro Ser
            260                 265                 270
Ala Tyr Ile Leu Gln Ser Glu Gly Ser Cys Ile Ser Gly Phe Gln Gly
            275                 280                 285
Met Asn Leu Pro Thr Glu Ser Gly Glu Leu Trp Ile Leu Gly Asp Val
        290                 295                 300
Phe Ile Arg Gln Tyr Phe Thr Val Phe Asp Arg Ala Asn Asn Gln Val
305                 310                 315                 320
Gly Leu Ala Pro Val Ala
                325
```

CATALYTICALLY ACTIVE RECOMBINANT MEMAPSIN AND METHODS OF USE THEREOF

This application claims priority to U.S. Ser. No. 60/141,363 filed Jun. 28, 1999 by Lin, et al., U.S. Ser. No. 60/168,060 filed Nov. 30, 1999 by Lin, et al., U.S. Ser. No. 60/177,836 filed Jan. 25, 2000 by Lin, et al., U.S. Ser. No. 60/178,368 filed Jan. 27, 2000 by Lin, et a., and U.S. Ser. No. 60/210,292 filed Jun. 8, 2000 by Lin Hong, et al., the teachings of which are incorporated by reference herein.

BACKGROUND OF THE INVENTION

This invention is in the area of the expression of catalytically active Memapsin 2 (beta-secretase) and use thereof in the design and screening of specific inhibitors which are useful in the treatment and/or prevention of Alzheimer's Disease.

Alzheimer's disease (AD) is a degenerative disorder of the brain first described by Alios Alzheimer in 1907 after examining one of his patients who suffered drastic reduction in cognitive abilities and had generalized dementia (*The early story of Alzheimer's Disease,* edited by Bick et al. (Raven Press, N.Y. 1987)). It is the leading cause of dementia in elderly persons. AD patients have increased problems with memory loss and intellectual functions which progress to the point where they cannot function as normal individuals. With the loss of intellectual skills the patients exhibit personality changes, socially inappropriate actions and schizophrenia (*A Guide to the Understanding of Alzheimer's Disease and Related Disorders,* edited by Jorm (New York University Press, New York 1987). AD is devastating for both victims and their families, for there is no effective palliative or preventive treatment for the inevitable neurodegeneration.

AD is associated with neuritic plaques measuring up to 200 µm in diameter in the cortex, hippocampus, subiculum, hippocampal gyrus, and amygdala. One of the principal constituents of neuritic plaques is amyloid, which is stained by Congo Red (Fisher (1983); Kelly Microbiol. Sci. 1(9):214–219 (1984)). Amyloid plaques stained by Congo Red are extracellular, pink or rust-colored in bright field, and birefringent in polarized light. The plaques are composed of polypeptide fibrils and are often present around blood vessels, reducing blood supply to various neurons in the brain.

Various factors such as genetic predisposition, infectious agents, toxins, metals, and head trauma have all been suggested as possible mechanisms of AD neuropathy. Available evidence strongly indicates that there are distinct types of genetic predispositions for AD. First, molecular analysis has provided evidence for mutations in the amyloid precursor protein (APP) gene in certain AD-stricken families (Goate et al. *Nature* 349:704–706 (1991); Murrell et al. *Science* 254:97–99 (1991); Chartier-Harlin et al. *Nature* 353:844–846 (1991); Mullan et al., *Nature Genet.* 1:345–347 (1992)). Additional genes for dominant forms of early onset AD reside on chromosome 14 and chromosome 1 (Rogaev et al., *Nature* 376:775–778 (1995); Levy-Lahad et al., *Science* 269:973–977 (1995); Sherrington et al., *Nature* 375:754–760 (1995)). Another loci associated with AD resides on chromosome 19 and encodes a variant form of apolipoprotein E (Corder, *Science* 261:921–923 (1993)).

Amyloid plaques are abundantly present in AD patients and in Down's Syndrome individuals surviving to the age of 40. The overexpression of APP in Down's Syndrome is recognized as a possible cause of the development of AD in Down's patients over thirty years of age (Rumble et al., *New England J. Med.* 320:1446–1452 (1989); Mann et al., *Neurobiol. Aging* 10:397–399 (1989)). The plaques are also present in the normal aging brain, although at a lower number. These plaques are made up primarily of the amyloid β peptide (Aβ; sometimes also referred to in the literature as β-amyloid peptide or β peptide) (Glenner and Wong, *Biochem. Biophys. Res. Comm.* 120:885–890 (1984)), which is also the primary protein constituent in cerebrovascular amyloid deposits. The amyloid is a filamentous material that is arranged in beta-pleated sheets. Aβ is a hydrophobic peptide comprising up to 43 amino acids.

The determination of its amino acid sequence led to the cloning of the APP cDNA (Kang et al., *Nature* 325:733–735 (1987); Goldgaber et al., *Science* 235:877–880 (1987); Robakis et al., *Proc. Natl. Acad. Sci.* 84:4190–4194 (1987); Tanzi et al., *Nature* 331:528–530 (1988)) and genomic APP DNA (Lemaire et al., *Nucl. Acids Res.* 17:517–522 (1989); Yoshikai et al., *Gene* 87, 257–263 (1990)). A number of forms of APP cDNA have been identified, including the three most abundant forms, APP695, APP751, and APP770. These forms arise from a single precursor RNA by alternate splicing. The gene spans more than 175 kb with 18 exons (Yoshikai et al. (1990)). APP contains an extracellular domain, a transmembrane region and a cytoplasmic domain. Aβ consists of up to 28 amino acids just outside the hydrophobic transmembrane domain and up to 15 residues of this transmembrane domain. Aβ is normally found in brain and other tissues such as heart, kidney and spleen. However, Aβ deposits are usually found in abundance only in the brain.

Van Broeckhaven et al., *Science* 248:1120–1122 (1990), have demonstrated that the APP gene is tightly linked to hereditary cerebral hemorrhage with amyloidosis (HCHWA-D) in two Dutch families. This was confirmed by the finding of a point mutation in the APP coding region in two Dutch patients (Levy et al., *Science* 248:1124–1128 (1990)). The mutation substituted a glutamine for glutamic acid at position 22 of the Aβ (position 618 of APP695, or position 693 of APP770). In addition, certain families are genetically predisposed to Alzheimer's disease, a condition referred to as familial Alzheimer's disease (FAD), through mutations resulting in an amino acid replacement at position 717 of the full length protein (Goate et al. (1991); Murrell et al. (1991); Chartier-Harlin et al. (1991)). These mutations co-segregate with the disease within the families and are absent in families with late-onset AD. This mutation at amino acid 717 increases the production of the $A\beta_{1-42}$ form of Aβ from APP (Suzuki et al., *Science* 264:1336–1340 (1994)). Another mutant form contains a change in amino acids at positions 670 and 671 of the full length protein (Mullan et al. (1992)). This mutation to amino acids 670 and 671 increases the production of total Aβ from APP (Citron et al., *Nature* 360:622–674 (1992)).

APP is processed in vivo at three sites. The evidence suggests that cleavage at the β-secretase site by a membrane associated metalloprotease is a physiological event. This site is located in APP 12 residues away from the lumenal surface of the plasma membrane. Cleavage of the β-secretase site (28 residues from the plasma membrane's lumenal surface) and the β-secretase site (in the transmembrane region) results in the 40/42-residue β-amyloid peptide (A β), whose elevated production and accumulation in the brain are the central events in the pathogenesis of Alzheimer's disease (for review, see Selkoe, D. J. *Nature* 399:23–31 (1999)). Presenilin 1, another membrane protein found in human brain, controls the hydrolysis at the APP (β-secretase site and has been postulated to be itself the responsible protease (Wolfe, M. S. et al., *Nature* 398:513–517 (1999)). Presenilin 1 is expressed as a single chain molecule and its processing by a protease, presenilinase, is required to prevent it from rapid degradation (Thinakaran, G. et al., *Neuron* 17:181–190 (1996) and Podlisny, M. B., et al., *Neurobiol. Dis.* 3:325–37 (1997)). The identity of presenilinase is unknown. The in vivo processing of the β-secretase site is thought to be the rate-limiting step in A β production (Sinha, S. & Lieberburg, I., *Proc. Natl. Acad. Sci., USA*, 96:11049–11053 (1999)), and is therefore a strong therapeutic target.

The design of inhibitors effective in decreasing amyeloid plaque formation is dependent on the identification of the critical enzyme(s) in the cleavage of APP to yield the 42 amino acid peptide, the $A\beta_{1-42}$ form of Aβ. Although several enzymes have been identified, it has not been possible to produce active enzyme. Without active enzyme, one cannot confirm the substrate specificity, determine the subsite specificity, nor determine the kinetics or critical active site residues, all of which are essential for the design of inhibitors.

Memapsin 2 has been shown to be beta-secretase, a key protease involved in the production in human brain of beta-amyloid peptide from beta-amyloid precursor protein (for review, see Selkoe, D. J. *Nature* 399:23–31 (1999)). It is now generally accepted that the accumulation of beta-amyloid peptide in human brain is a major cause for the Alzheimer's disease. Inhibitors specifically designed for human memapsin 2 should inhibit or decrease the formation of beta-amyloid peptide and the progression of the Alzheimer's disease.

Memapsin 2 belongs to the aspartic protease family. It is homologous in amino acid sequence to other eukaryotic aspartic proteases and contains motifs specific to that family. These structural similarities predict that memapsin 2 and other eukaryotic aspartic proteases share common catalytic mechanism Davies, D. R., *Annu. Rev. Biophys. Chem.* 19, 189 (1990). The most successful inhibitors for aspartic proteases are mimics of the transition state of these enzymes. These inhibitors have substrate-like structure with the cleaved planar peptide bond between the carbonyl carbon and the amide nitrogen replaced by two tetrahedral atoms, such as hydroxyethylene [—CH(OH)—CH$_2$—], which was originally discovered in the structure of pepstatin (Marciniszyn et al., 1976).

However, for clinical use, it is preferable to have small molecule inhibitors which will pass through the blood brain barrier and which can be readily synthesized. It is also desirable that the inhibitors are relatively inexpensive to manufacture and that they can be administered orally. Screening of thousands of compounds for these properties would require an enormous effort. To rationally design memapsin 2 inhibitors for treating Alzheimer's disease, it will be important to know the three-dimensional structure of memapsin 2, especially the binding mode of an inhibitor in the active site of this protease.

It is therefore an object of the present invention to provide purified, recombinant, and active memapsin 2, as well as its substrate and subsite specificity and critical active site residues.

It is a further object of the present invention to provide compositions and methods for synthesis of inhibitors of memapsin 2.

It is a still further object of the present invention to provide compositions that interact with memapsin 2 or its substrate to inhibit cleavage by the memapsin 2 which can cross the blood brain barrier (BBB).

It is therefore an object of the present invention to provide means for rational design and screening of compounds for inhibition of mamapsin 2.

SUMMARY OF THE INVENTION

Methods for the production of purified, catalytically active, recombinant memapsin 2 have been developed. The substrate and subsite specificity of the catalytically active enzyme have been determined. The active enzyme and assays for catalytic activity are useful in screening libraries for inhibitors of the enzyme.

The substrate and subsite specificity information was used to design substrate analogs of the natural memapsin 2 substrate that can inhibit the function of memapsin 2. The substrate analogs are based on peptide sequences, shown to be related to the natural peptide substrates for memapsin 2. The substrate analogs contain at least one analog of an amide (peptide) bond which is not capable of being cleaved by memapsin 2. Processes for the synthesis of two substrate analogues including isosteres at the sites of the critical amino acid residues were developed and the substrate analogues, OMR99-1 and OM99-2, were synthesized. OM99-2 is based on an octapeptide Glu-Val-Asn-Leu-Ala-Ala-Glu-Phe (SEQ ID NO:28) with the Leu-Ala peptide bond substituted by a transition-state isostere hydroxyethylene group. The inhibition constant of OM99-2 is $1.6 \times 10^{-9}$ M against recombinant pro-memapsin 2. Crystallography of memapsin 2 bound to this inhibitor was used to determine the three dimensional structure of the protein, as well as the importance of the various residues in binding.

This information can be used by those skilled in the art to design new inhibitors, using commercially available software programs and techniques familiar to those in organic chemistry and enzymology, to design new inhibitors. For example, the side chains of the inhibitors may be modified to produce stronger interactions (through hydrogen bonding, hydrophobic interaction, charge interaction and/or van der Waal interaction) in order to increase inhibition potency. Based on this type of information, the residues with minor interactions may be eliminated from the new inhibitor design to decrease the molecular weight of the inhibitor. The side chains with no structural hindrance from the enzyme may be cross-linked to lock in the effective inhibitor conformation. This type of structure also enables the design of peptide surrogates which may effectively fill the binding sites of memapsin 2 yet produce better pharmaceutical properties.

The examples demonstrate the production of catalytically active enzyme, design and synthesis of inhibitors, and how the crystal structure was obtained. The examples thereby demonstrate how the methods and materials described herein can be used to screen libraries of compounds for other inhibitors, as well as for design of inhibitors. These inhibitors are useful in the prevention and/or treatment of Alzheimer's disease as mediated by the action of the beta secretase memapsin 2, in cleaving APP.

BRIEF DESCRIPTION OF THE DRAWINGS

FIG. 1 depicts the plasmid construct of vector pET-1 la-memapsin 2-T1 and pET-11a-memapsin 2-T2. The T7 promotor, amino acid sequence from the vector (T7 protein) (SEQ ID NO:3), and the beginning and ending of the memapsin 2 T1 and T2 construct are shown. Construct pro-memapsin 2-T1 was used in the preparation of protein for crystallization and includes residues 1v-15v which are derived from vector pET-11a. Residues 1p-48p are putative pro-peptide. Residues 1-393 correspond to the mature protease domain and C-terminal extension. The residue numbering of memapsin 2 starts at the aligned N-terminal position of pepsin (FIG. 3).

FIGS. 5A–E are photographs of crystals of recombinant memapsin 2-OM99-2 complex.

DETAILED DESCRIPTION OF THE INVENTION

Figure 2A:
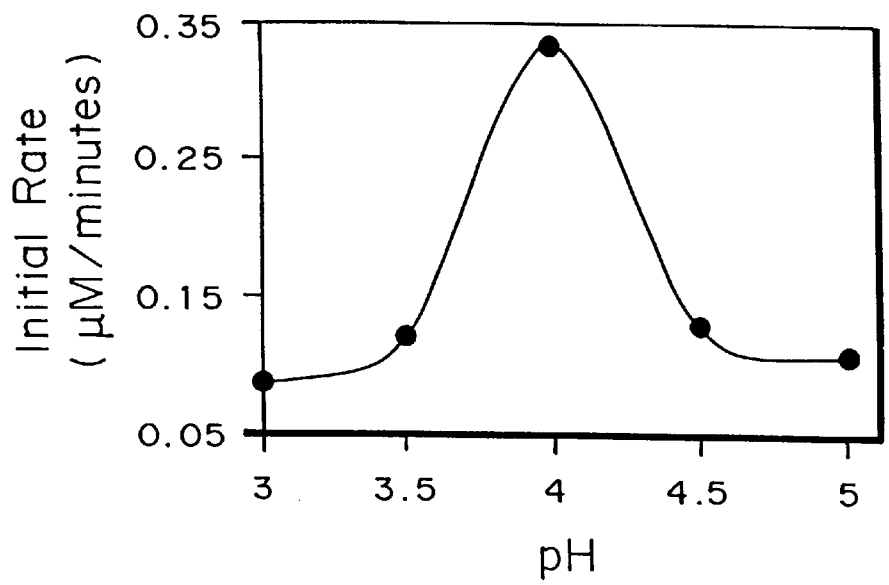
FIG. 2A is a graph of the initial rate of hydrolysis of synthetic peptide swAPP (see Table 1) by $M2_{pd}$ at different pH.

I. Preparation of Catalytically Active Recombinant Memapsin 2

Cloning and Expression of Memapsin 2

Memapsin 2 was cloned and the nucleotide (SEQ ID NO. 1) and predicted amino acid (SEQ ID NO. 2) sequences were determined, as described in Example 1. The cDNA was assembled from the fragments. The nucleotide and the deduced protein sequence are shown in SEQ ID NOs. 1 and 2, respectively. The protein is the same as the aspartic proteinase 2 (ASP2) described in EP 0 855 444 A by SmithKline Beecham Pharmaceuticals, (published Jul. 29, 1998), and later reported by Sinha, et al., *Nature* 402, 537–540 (December 1999) and Vassar, et al., *Science* 286, 735–741 (Oct. 22, 1999).

Pro-memapsin 2 is homologous to other human aspartic proteases. Based on the alignments, Pro-memapsin 2 contains a pro region, an aspartic protease region, and a trans-membrane region near the C-terminus. The C-terminal domain is over 80 residues long. The active enzyme is memapsin 2 and its pro-enzyme is pro-memapsin 2.

Refolding Catalytically Active Enzyme

In order to determine the substrate specificity and to design inhibitors, it is necessary to express catalytically active recombinant enzyme. No other known proteases contain a transmembrane domain. The presence of trans-membrane domains makes the recombinant expression of these proteins less predictable and more difficult. The transmembrane region often needs to be removed so that secretion of the protein can take place. However, the removal of the transmembrane region can often alter the structure and/or function of the protein.

The starting assumption was that the region of memapsin 2 that is homologous with other aspartic proteases would independently fold in the absence of the transmembrane domain, and would retain protease activity in the absence of the C-terminal transmembrane region. The transmembrane region appears to serve as a membrane anchor. Since the active site is not in the transmembrane region and activity does not require membrane anchoring, memapsin 2 was expressed in *E. coli* in two different lengths, both without the transmembrane region, and purified, as described in Example 3. The procedures for the culture of transfected bacteria, induction of synthesis of recombinant proteins and the recovery and washing of inclusion bodies containing recombinant proteins are essentially as described by Lin et al., (1994). Refolding was not a simple matter, however. Two different refolding methods both produced satisfactory results. In both methods, the protein was dissolved in a strong denaturing/reducing solution such as 8M urea/100 mM beta-mercaptoethanol. The rate at which the protein was refolded, and in what solution, was critical to activity. In one method, the protein is dissolved into 8M urea/100 mM beta-mercaptoethanol then rapidly diluted into 20 volumes of 20 mM-Tris, pH 9.0, which is then slowly adjusted to pH 8 with 1M HCl. The refolding solution was then kept at 4° C. for 24 to 48 hours before proceeding with purification. In the second method, an equal volume of 20 mM Tris, 0.5 mM oxidized/1.25 mM reduced glutathione, pH 9.0 is added to rapidly stirred pro-memapsin 2 in 8M urea/10 mM beta-mercaptoethanol. The process is repeated three more times with 1 hour intervals. The resulting solution is then dialyzed against sufficient volume of 20 mM Tris base so that the final urea concentration is 0.4M. The pH of the solution is then slowly adjusted to 8.0 with 1M HCl.

The refolded protein is then further purified by column chromatography, based on molecular weight exclusion, and/or elution using a salt gradient, and analyzed by SDS-PAGE analysis under reduced and non-reduced conditions.

II. Substrate Specificity and Enzyme Kinetics of Memapsin 2

Substrate Specificity

The tissue distribution of the memapsin 2 was determined, as described in Example 2. The presence of memapsin 2 (M2) in the brain indicated that it might hydrolyze the β-amyloid precursor protein (APP). As described below, detailed enzymatic and cellular studies demonstrated that M2 fits all the criteria of the β-secretase.

The M2 three-dimensional structure modeled as a type I integral membrane protein. The model suggested that its globular protease unit can hydrolyze a membrane anchored polypeptide at a distance range of 20–30 residues from the membrane surface. As a transmembrane protein of the brain, APP is a potential substrate and its beta-secretase site, located about 28 residues from the plasma membrane surface, is within in the range for M2 proteolysis.

A synthetic peptide derived from this site (SEVKM/DAEFR) (SEQ ID NO:4) was hydrolyzed by $M2_{pd}$ (modified M2 containing amino acids from $Ala^{-8P}$ to $Ala^{326}$) at the beta-secretase site (marked by /). A second peptide (SEVNL/DAEFR) (SEQ ID NO:5) derived from the APP beta-secretase site and containing the 'Swedish mutation' (Mullan, M. et al., *Nature Genet.* 2:340–342 (1992)), known to elevate the level of alpha-beta production in cells (Citron, M. et al., *Nature* 260:672–674 (1992)), was hydrolyzed by $M2_{pd}$ with much higher catalytic efficiency. Both substrates were optimally cleaved at pH 4.0. A peptide derived from the processing site of presenilin 1 (SVNM/AEGD) (SEQ ID NO:6) was also cleaved by $M2_{pd}$ with less efficient kinetic parameters. A peptide derived from the APP gamma-secretase site (KGGVVIATVIVK) (SEQ ID NO:7) was not cleaved by $M^2_{pd}$. Pepstatin A inhibited $M2_{pd}$ poorly ($IC_{50}$ approximately approximately 0.3 mM). The kinetic parameters indicate that both presenilin 1 ($k_{cat}$, 0.67 $s^{-1}$; Km, 15.2 mM; $k_{cat}/K_m$, 43.8 $s^{-1}M^{-1}$) and native APP peptides ($k_{cat}/K_m$, 39.9 $s^{-1}M^{-1}$) are not as good substrates as the Swedish APP peptide ($k_{cat}$, 2.45 $s^{-1}$, $K_m$, 1 mM; $k_{cat}/K_m$, 2450 $s^{-1}M^{-1}$).

To determine if M2 possesses an APP beta-secretase function in mammalian cells, memapsin 2 was transiently expressed in HeLa cells (Lin, X., et al., *FASEB J* 7:1070–1080 (1993)), metabolically pulse-labeled with $^{35}$S-Met, then immunoprecipitated with anti-APP antibodies for visualization of APP-generated fragments after SDS-polyacrylamide electrophoresis and imaging. SDS-PAGE patterns of immuno-precipitated APP NB-fragment (97 kD band) from the conditioned media (2 h) of pulse-chase experiments showed that APP was cleaved by M2. Controls transfected with APP alone and co-transfected with APP and M2 with Bafilomycin Al added were performed. SDS-PAGE patterns of APP BC-fragment (12 kD) were immunoprecipitated from the conditioned media of the same experiment as discussed above. Controls transfected with APP alone; co-transfected with APP and M2; co-transfected with APP and M2 with Bafilomycin A1; transfections of Swedish APP; and co-transfections of Swedish APP and M2 were performed. SDS-PAGE gels were also run of immunoprecipitated M2 (70 kD), M2 transfected cells; untransfected HeLa cells after long time film exposure; and endogenous M2 from HEK 293 cells. SDS-PAGE patterns of APP fragments (100 kD betaN-fragment and 95 kD betaN-fragment) recovered from conditioned media after immunoprecipitation using antibodies specific for different APP regions indicated that memapsin 2 cleaved APP.

Cells expressing both APP and M2 produced the 97 kD APP beta N-fragment (from the N-terminus to the beta-secretase site) in the conditioned media and the 12 kD betaC-fragment (from the beta-secretase site to the C-terminus) in the cell lystate. Controls transfected with APP alone produced little detectable betaN-fragment and no beta C-fragment. Bafilomycin A1, which is known to raise the intra-vesicle pH of lysosomes/endosomes and has been shown to inhibit APP cleavage by beta-secretase (Knops, J. et al., *J. Biol. Chem.* 270:2419–2422 (1995)), abolished the production of both APP fragments beta N- and beta C- in co-transfected cells. Cells transfected with Swedish APP alone did not produce the beta C-fragment band in the cell lysate but the co-transfection of Swedish APP and M2 did. This Swedish beta C-fragment band is more intense than that of wild-type APP. A 97-kD beta N-band is also seen in the conditioned media but is about equal intensity as the wild-type APP transfection.

These results indicate that M2 processes the beta-secretase site of APP in acidic compartments such as the endosomes. To establish the expression of transfected M2 gene, the pulse-labeled cells were lysed and immunoprecipitated by anti-M2 antibodies. A 70 kD M2 band was seen in cells transfected with M2 gene, which has the same mobility as the major band from HEK 293 cells known to express beta-secretase (Citron, M. et al., *Nature* 260:672–674 (1992)). A very faint band of M2 is also seen, after a long film exposure, in untransfected HeLa cells, indicating a very low level of endogenous M2, which is insufficient to produce betaN- or betaC-fragments without M2 transfection. Antibody alpha-$beta_{1-17}$, which specifically recognizes residues 1–17 in alpha-beta peptide, was used to confirm the correct beta-secretase site cleavage. In cells transfected with APP and M2, both beta N- and beta N-fragments are visible using an antibody recognizing the N-terminal region of APP present in both fragments. Antibody $Abeta_{1-17}$ recognize the beta N-fragment produced by endogenous beta-secretase in the untransfected cells. This antibody was, however, unable to recognize the betaN-fragment known to be present in cells co-transfected with APP and M2. These observations confirmed that betaN-fragment is the product of beta-secretase site cut by M2, which abolished the recognition epitope of alpha-$beta_{1-17}$.

The processing of APP by M2 predicts the intracellular colocalization of the two proteins. HeLa cells co-expressing APP and M2 were stained with antibodies directed toward APP and M2 and visualized simultaneously by CSLM using a 100x objective. Areas of colocalization appeared in yellow.

Immunodetection observed by confocal microscopy of both APP and M2 revealed their colocalization in the superimposed scans. The distribution of both proteins is consistent with their residence in lysosomal/endosomal compartments.

In specificity studies, it was found that $M2_{pd}$ cleaved its pro peptide (2 sites) and the protease portion (2 sites) during a 16 h incubation after activation (Table 1). Besides the three peptides discussed above, $M2_{pd}$ also cleaved oxidized bovine insulin B chain and a synthetic peptide Nch. Native proteins were not cleaved by $M2_{pd}$.

The data indicate that human M2 fulfills all the criteria of a beta-secretase which cleaves the beta-amyloid precursor protein (APP): (a) M2 and APP are both membrane proteins present in human brain and co-localize in mammalian cells, (b) M2 specifically cleaves the beta-secretase site of synthetic peptides and of APP in cells, (c) M2 preferentially cleaves the beta-secretase site from the Swedish over the wild-type APP, and (d) the acidic pH optimum for M2 activity and bafilomycin A1 inhibition of APP processing by M2 in the cells are consistent with the previous observations that beta-secretase cleavage occurs in acidic vesicles (Knops, J., et al., *J. Biol. Chem.* 270:2419–2422 (1995)). The spontaneous appearance of activity of recombinant pro-M2 in an acidic solution suggests that, intracellularly, this zymogen can by itself generate activity in an acidic vesicle like an endosome.

II. Design and Synthesis of Inhibitors

Design of Substrate Analogs for Memapsin 2.

The five human aspartic proteases have homologous amino acid sequences and have similar three-dimensional structures. There are two aspartic residues in the active site and each residue is found within the signature aspartic protease sequence motif, Asp-Thr/Ser-Gly- (SEQ ID NO:8). There are generally two homologous domains within an aspartic protease and the substrate binding site is positioned between these two domains, based on the three-dimensional structures. The substrate binding sites of aspartic proteases generally recognize eight amino acid residues. There are generally four residues on each side of the amide bond which is cleaved by the aspartic protease.

Typically the side chains of each amino acid are involved in the specificity of the substrate/aspartic protease interaction. The side chain of each substrate residue is recognized by regions of the enzyme which are collectively called sub-sites. The generally accepted nomenclature for the protease sub-sites and their corresponding substrate residues are shown below, where the double slash represents the position of bond cleavage.

Protease sub-sites S4 S3 S2 S1 S1' S2' S3' S4'
Substrate residues P4 P3 P2 P1 I P1' P2' P3' P4'

While there is a general motif for aspartic protease substrate recognition, each protease has a very different substrate specificity and breadth of specificity. Once the specificity of an aspartic protease is known, inhibitors can be designed based on that specificity, which interact with the aspartic protease in a way that prevents natural substrate from being efficiently cleaved. Some aspartic proteases have specificities which can accommodate many different residues in each of the sub-sites for successful hydrolysis. Pepsin and cathepsin D have this type of specificity and are said to have "broad" substrate specificity. When only a very few residues can be recognized at a sub-site, such as in renin, the aspartic protease is said to have a stringent or narrow specificity.

The information on the specificity of an aspartic protease can be used to design specific inhibitors in which the preferred residues are placed at specific sub-sites and the cleaved peptide bond is replaced by an analog of the transition-state. These analogs are called transition state isosteres. Aspartic proteases cleave amide bonds by a hydrolytic mechanism. This reaction mechanism involves the attack by a hydroxide ion on the β-carbon of the amino acid. Protonation must occur at the other atom attached to the β-carbon through the bond that is to be cleaved. If the β-carbon is insufficiently electrophilic or the atom attached to the bond to be cleaved is insufficiently nucleophilic the bond will not be cleaved by a hydrolytic mechanism. Analogs exist which do not mimic the transition state but which are non-hydrolyzable, but transition state isosteres mimic the transition state specifically and are non-hydrolyzable.

Transition state theory indicates that it is the transition state intermediate of the reaction which the enzyme catalyzes for which the enzyme has its highest affinity. It is the transition state structure, not the ground state structure, of the substrate which will have the highest affinity for its given enzyme. The transition state for the hydrolysis of an amide bond is tetrahedral while the ground state structure is planar. A typical transition-state isostere of aspartic protease is —CH(OH)—CH$_2$—, as was first discovered in pepstatin by Marciniszyn et al. (1976). The transition-state analogue principles have been successfully applied to inhibitor drugs for human immunodeficiency virus protease, an aspartic protease. Many of these are currently in clinical use. Information on the structure, specificity, and types of inhibitors can be found in Tang, Acid Proteases, Structure, Function and Biology, Adv. in Exptl. Med. Biol. vol. 95 (Plenum Press, N.Y. 1977); Kostka, Aspartic Proteinases and their Inhibitors (Walter de Gruyter, Berlin 1985); Dunn, Structure and Functions of the Aspartic Proteinases, Adv. in Exptl. Med. Biol. 306 (Plenum Press, N.Y. 1991); Takahashi, Aspartic Proteases, Structure, Function, Biology, Biomedical Implications, Adv. in Exptl. Med. Biol. 362 (Plenum Press, N.Y. 1995); and James, Aspartic Proteinases, Retroviral and Cellular Enzymes, Adv. in Exptl. Med. Biol. 436 (Plenum Press, N.Y. 1998)).

Substrate analog compositions are generally of the general formula X-L$_4$-P$_4$- L$_3$-P$_3$-L$_2$-P$_2$-L$_1$-P$_1$-L$_0$-P$_1$'-L$_1$'-P$_2$'-L$_2$'-P$_3$'-L$_3$'-P$_4$'L$_4$'-Y. The substrate analog compositions are analogs of small peptide molecules. Their basic structure is derived from peptide sequences that were determined through structure/function studies. It is understood that positions represented by P$_X$ represent the substrate specificity position relative to the cleavage site which is represented by an —L$_0$—. The positions of the compositions represented by L$_X$ represent the linking regions between each substrate specificity position, P$_X$.

In a natural substrate for memapsin 2, a P$_X$-L$_X$ pair would represent a single amino acid of the peptide which is to be cleaved. In the present general formula, each P$_X$ part of the formula refers to the α-carbon and side chain functional group of each would be amino acid. Thus, the P$_X$ portion of an P$_X$-L$_X$ pair for alanine represents HC—CH$_3$. The general formula representing the P$_X$ portion of the general composition is —R$_1$CR$_3$—.

In general R$_1$ can be either CH$_3$ (side chain of alanine), CH(CH$_3$)$_2$ (side chain of valine), CH$_2$CH(CH$_3$)$_2$ (side chain of leucine), (CH$_3$)CH(CH$_2$ CH$_3$) (side chain of isoleucine), CH$_2$(Indole) (side chain of tryptophan), CH$_2$(Benzene) (side chain of phenylalanine), CH$_2$CH$_2$SCH$_3$ (side chain of methionine), H (side chain of glycine), CH$_2$OH (side chain of serine), CHOHCH$_3$ (side chain of threonine), CH$_2$(Phenol) (side chain of tyrosine), CH$_2$SH (side chain of cysteine), CH$_2$CH$_2$CONH$_2$ (side chain of glutamine), CH$_2$CONH$_2$ (side chain of asparagine), CH$_2$CH$_2$CH$_2$CH$_2$NH$_2$ (side chain of lysine), CH$_2$CH$_2$CH$_2$NHC(NH)(NH$_2$) (side chain of arginine), CH$_2$(Imidazole) (side chain of histidine), CH$_2$COOH (side chain of aspartic acid), CH$_2$CH$_2$COOH (side chain of glutamic acid), and functional natural and non-natural derivatives or synthetic substitutions of these.

It is most preferred that R$_3$ is a single H. In general, however, R$_3$ can be alkenyl, alkynal, alkenyloxy, and alkynyloxy groups that allow binding to memapsin 2. Preferably, alkenyl, alkynyl, alkenyloxy and alkynyloxy groups have from 2 to 40 carbons, and more preferably from 2 to 20 carbons, from 2 to 10 carbons, or from 2 to 3 carbons., and functional natural and non-natural derivatives or synthetic substitutions of these.

The $L_X$ portion of the $P_X$-$L_X$ pair represents the atoms linking the $P_X$ regions together. In a natural substrate the $L_X$ represents the β-carbon attached to the amino portion of what would be the next amino acid in the chain. Thus, $L_X$ would be represented by —CO—NH—. The general formula for $L_X$ is represented by $R_2$. In general $R_2$ can be CO-HN (amide), CH(OH)(CH$_2$) (hydroxyethylene), CH(OH)CH(OH) (dihydroxyethylene), CH(OH)CH$_2$NH (hydroxyethylamine), PO(OH)CH$_2$ (phosphinate), CH$_2$NH, (reduced amide). It is understood that more than one L- maybe an isostere as long as the substrate analog functions to inhibit aspartic protease function.

Ls which are not isosteres may either be an amide bond or mimetic of an amide bond that is non-hydrolyzable.

X and Y represent molecules which are not typically involved in the recognition by the aspartic protease recognition site, but which do not interfere with recognition. It is preferred that these molecules confer resistance to the degradation of the substrate analog. Preferred examples would be amino acids coupled to the substrate analog through a non-hydrolyzable bond. Other preferred compounds would be capping agents. Still other preferred compounds would be compounds which could be used in the purification of the substrate analogs such as biotin.

As used herein, alkyl refers to substituted or unsubstituted straight, branched or cyclic alkyl groups; and alkoxyl refers to substituted or unsubstituted straight, branched or cyclic alkoxy. Preferably, alkyl and alkoxy groups have from 1 to 40 carbons, and more preferably from 1 to 20 carbons, from 1 to 10 carbons, or from 1 to 3 carbons.

As used herein, alkenyl refers to substituted or unsubstituted straight chain or branched alkenyl groups; alkynyl refers to substituted or unsubstituted straight chain or branched alkynyl groups; alkenyloxy refers to substituted or unsubstituted straight chain or branched alkenyloxy; and alkynyloxy refers to substituted or unsubstituted straight chain or branched alkynyloxy. Preferably, alkenyl, alkynyl, alkenyloxy and alkynyloxy groups have from 2 to 40 carbons, and more preferably from 2 to 20 carbons, from 2 to 10 carbons, or from 2 to 3 carbons.

As used herein, alkaryl refers to an alkyl group that has an aryl substituent; aralkyl refers to an aryl group that has an alkyl substituent; heterocyclic-alkyl refers to a heterocyclic group with an alkyl substituent; alkyl-heterocyclic refers to an alkyl group that has a heterocyclic substituent.

The substituents for alkyl, alkenyl, alkynyl, alkoxy, alkenyloxy, and alkynyloxy groups can be halogen, cyano, amino, thio, carboxy, ester, ether, thioether, carboxamide, hydroxy, or mercapto. Further, the groups can optionally have one or more methylene groups replaced with a heteroatom, such as O, NH or S.

A number of different substrates were tested and analyzed, and the cleavage rules for Memapsin 2 were determined. The results of the substrates which were analyzed are presented in Table 1 and the rules determined from these results are summarized below.

(1) The primary specificity site for a memapsin 2 substrate is subsite position, $P_1$'. This means that the most important determinant for substrate specificity in memapsin 2 is the amino acid, S1'. $P_1$' must contain a small side chain for memapsin 2 to recognize the substrate. Preferred embodiments are substrate analogs where $R_1$ of the $P_1$' position is either H (side chain of glycine), CH$_3$ (side chain of alanine), CH$_2$OH (side chain of serine), or CH$_2$OOH (side chain of aspartic acid). Embodiments that have an R1 structurally smaller than CH$_3$ (side chain of alanine) or CH$_2$OH (side chain of serine) are also preferred.

(2) There are no specific sequence requirements at positions $P_4$, $P_3$, $P_2$, $P_1$, $P_2$', $P_3$', and $P_4$' Each site can accommodate any other amino acid residue in singularity as long as rule number 3 is met.

(3) At least two of the remaining seven positions, $P_4$, $P_3$, $P_2$, $P_1$, $P_2$', $P_3$', and $P_4$', must have an $R_1$ which is made up of a hydrophobic residue. It is preferred that there are at least three hydrophobic residues in the remaining seven positions, $P_4$, $P_3$, $P_2$, $P_1$, $P_2$', $P_3$', and $P_4$'. Preferred $R_1$ groups for the positions that contain a hydrophobic group are CH$_3$ (side chain of alanine), CH(CH$_3$)$_2$ (side chain of valine), CH$_2$CH(CH$_3$)$_2$ (side chain of leucine), (CH$_3$)CH(CH$_2$ CH$_3$) (side chain of isoleucine), CH$_2$(INDOLE) (side chain of tryptophan), CH$_2$(Benzene) (side chain of phenylalanine), CH$_2$CH$_2$SCH$_3$ (side chain of methionine) CH$_2$(Phenol) (side chain of tyrosine). It is more preferred that the hydrophobic group be a large hydrophobic group. Preferred $R_1$s which contain large hydrophobic groups are CH(CH$_3$)$_2$ (side chain of valine), CH$_2$CH(CH$_3$)$_2$ (side chain of leucine), (CH$_3$)CH(CH$_2$ CH$_3$) (side chain of isoleucine), CH$_2$(Indole) (side chain of tryptophan), CH$_2$(Benzene) (side chain of phenylalanine), CH$_2$CH$_2$SCH$_3$ (side chain of methionine) CH$_2$(Phenol) (side chain of tyrosine). It is most preferred that positions with a hydrophobic $R_1$ are CH(CH$_3$)$_2$ (side chain of valine), CH$_2$CH(CH$_3$)$_2$ (side chain of leucine), CH$_2$(Benzene) (side chain of phenylalanine), CH$_2$CH$_2$SCH$_3$ (side chain of methionine), or CH$_2$(Phenol) (side chain of tyrosine).

(4) None of the eight positions, $P_4$, $P_3$, $P_2$, $P_1$, $P_1$,' $P_2$', $P_3$', and $P_4$' may have a proline side chain at its $R_1$ position.

(5) Not all subsites must have an P represented in the analog. For example, a substrate analog could have X-$P_2$-$L_1$-$P_1$-$L_0$-$P_1$'-$L_1$'-$P_2$'-$L_2$'-$P_3$'-$L_3$'-Y or it could have X-$L_1$-$P_1$-$L_0$-$P_1$'-$L_2$'-$P_2$'-$L_2$'-$P_3$'-$L_3$'-$P_4$'$L_4$'-Y.

Preferred substrate analogs are analogs having the sequences disclosed in Table 1, with the non-hydrolyzable analog between P1 and P1'.

Combinatorial Chemistry to Make Inhibitors

Combinatorial chemistry includes but is not limited to all methods for isolating molecules that are capable of binding either a small molecule or another macromolecule. Proteins, oligonucleotides, and polysaccharides are examples of macromolecules. For example, oligonucleotide molecules with a given function, catalytic or ligand-binding, can be isolated from a complex mixture of random oligonucleotides in what has been referred to as "in vitro genetics" (Szostak, TIBS 19:89, 1992). One synthesizes a large pool of molecules bearing random and defined sequences and subjects that complex mixture, for example, approximately $10^{15}$ individual sequences in 100 μg of a 100 nucleotide RNA, to some selection and enrichment process. Through repeated cycles of affinity chromatography and PCR amplification of the molecules bound to the ligand on the column, Ellington and Szostak (1990) estimated that 1 in $10^{10}$ RNA molecules folded in such a way as to bind a small molecule dyes. DNA molecules with such ligand-binding behavior have been isolated as well (Ellington and Szostak, 1992; Bock et al, 1992).

Techniques aimed at similar goals exist for small organic molecules, proteins and peptides and other molecules known to those of skill in the art. Screening sets of molecules for a desired activity whether based on libraries of small synthetic molecules, oligonucleotides, proteins or peptides is broadly referred to as combinatorial chemistry.

There are a number of methods for isolating proteins either have de novo activity or a modified activity. For example, phage display libraries have been used for a number of years. A preferred method for isolating proteins that have a given function is described by Roberts and Szostak (Roberts R. W. and Szostak J. W. Proc. Natl. Acad. Sci. USA, 94(23)12997–302 (1997). Another preferred method for combinatorial methods designed to isolate peptides is described in Cohen et al. (Cohen B. A., et al., Proc. Natl. Acad. Sci. USA 95(24): 14272–7 (1998)). This method utilizes a modified two-hybrid technology. Yeast two-hybrid systems are useful for the detection and analysis of protein-:protein interactions. The two-hybrid system, initially described in the yeast *Saccharomyces cerevisiae,* is a powerful molecular genetic technique for identifying new regulatory molecules, specific to the protein of interest (Fields and Song, *Nature* 340:245–6 (1989)). Cohen et al., modified this technology so that novel interactions between synthetic or engineered peptide sequences could be identified which bind a molecule of choice. The benefit of this type of technology is that the selection is done in an intracellular environment. The method utilizes a library of peptide molecules that attach to an acidic activation domain. A peptide of choice, for example an extracellular portion of memapsin 2 is attached to a DNA binding domain of a transcriptional activation protein, such as Gal 4. By performing the Two-hybrid technique on this type of system, molecules that bind the extracellular portion of memapsin 2 can be identified.

Screening of Small Molecule Libraries

In addition to these more specialized techniques, methodology well known to those of skill in the art, in combination with various small molecule or combinatorial libraries, can be used to isolate and characterize those molecules which bind to or interact with the desired target, either memapsin 2 or its substrate. The relative binding affinity of these compounds can be compared and optimum inhibitors identified using competitive or non-competitive binding studies which are well known to those of skill in the art. Preferred competitive inhibitors are non-hydrolyzable analogs of memapsin 2. Another will cause allosteric rearrangements which prevent memapsin 2 from functioning or folding correctly.

Computer assisted Rational Drug Design

Another way to isolate inhibitors is through rational design. This is achieved through structural information and computer modeling. Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. For example, using NMR spectroscopy, Inouye and coworkers were able to obtain the structural information of N-terminal truncated TSHK (transmembrane sensor histidine kinases) fragments which retain the structure of the individual sub-domains of the catalytic site of a TSHK. On the basis of the NMR study, they were able to identify potential TSHK inhibitors (U.S. Pat. No. 6,077,682 to Inouye). Another good example is based on the three-dimensional structure of a calcineurin/FKBP12/FK506 complex determined using high resolution X-ray crystallography to obtain the shape and structure of both the calcineurin active site binding pocket and the auxiliary FKBP12/FK506 binding pocket (U.S. Pat. No. 5,978,740 to Armistead). With this information in hand, researchers can have a good understanding of the association of natural ligands or substrates with the binding pockets of their corresponding receptors or enzymes and are thus able to design and make effective inhibitors.

Prediction of molecule-compound interaction when small changes are made in one or both requires molecular mechanics software and computationally intensive computers, usually coupled with user-friendly, menu-driven interfaces between the molecular design program and the user. Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 *Acta Pharmaceutica Fennica* 97, 159–166; Ripka, *New Scientist* 54–57 (Jun. 16, 1988); McKinaly and Rossmann, 1989 *Annu. Rev. Pharmacol. Toxiciol.* 29, 111–122; Perry and Davies, *QSAR: Quantitative Structure-Activity Relationships in Drug Design* pp. 189–193 (Alan R. Liss, Inc. 1989); Lewis and Dean, 1989 *Proc. R. Soc. Lond.* 236, 125–140 and 141–162; and, with respect to a model enzyme for nucleic acid components, Askew, et al., 1989 *J. Am. Chem. Soc.* 111, 1082–1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario.

Although described above with reference to design and generation of compounds which could alter binding, one could also screen libraries of known compounds, including natural products or synthetic chemicals, and biologically active materials, including proteins, for compounds which alter substrate binding or enzymatic activity.

Screening of Libraries

Design of substrate analogs and rational drug design are based on knowledge of the active site and target, and utilize computer software programs that create detailed structures of the enzyme and its substrate, as well as ways they interact, alone or in the presence of inhibitor. These techniques are significantly enhanced with x-ray crystallographic data in hand. Inhibitors can also be obtained by screening libraries of existing compounds for those which inhibit the catalytically active enzyme. In contrast to reports in the literature relating to memapsin 2, the enzyme described herein has activity analogous to the naturally produced enzyme, providing a means for identifying compounds which inhibit the endogenous activity. These potential inhibitors are typically identified using high throughput assays, in which enzyme, substrate (preferably a chromogenic substrate) and potential inhibitor (usually screened across a range of concentrations) are mixed and the extent of cleavage of substrate determined. Potentially useful inhibitors are those which decrease the amount of cleavage.

III. Methods of diagnosis and treatment

Inhibitors can be used in the diagnosis and treatment and/or prevention of Alzheimer's disease and conditions associated therewith, such as elevated levels of the forty-two amino acid peptide cleavage product, and the accumulation of the peptide in amyloid plaques.

Diagnostic Uses

The substrate analogs can be used as reagents for specifically binding to memapsin 2 or memapsin 2 analogs and for aiding in memapsin 2 isolation and purification or characterization, as described in the examples. The inhibitors and purified recombinant enzyme can be used in screens for those individuals more genetically prone to develop Alzheimer's disease.

Therapeutic Uses

Recombinant human memapsin 2 cleaves a substrate with the sequence LVNM/AEGD (SEQ ID NO:9). This sequence is the in vivo processing site sequence of human presenilins. Both presenilin 1 and presenilin 2 are integral membrane proteins. They are processed by protease cleavage, which removes the N terminal sequence from the unprocessed form. Once processed, presenilin forms a two-chain heterodimer (Capell et al., J. Biol. Chem. 273, 3205 (1998); Thinakaran et al., Neurobiol. Dis. 4, 438 (1998); Yu et al., Neurosci Lett. 2;254(3):125–8 (1998)), which is stable relative to the unprocessed presenilins. Unprocessed presenilines are quickly degraded (Thinakaran et al., J. Biol. Chem. 272, 28415 (1997); Steiner et al., J. Biol. Chem. 273, 32322 (1998)). It is known that presenilin controls the in vivo activity of beta-secretase, which in turn cleaves the amyloid precursor protein (APP) leading to the formation of alpha-beta42. The accumulation of alpha-beta42 in the brain cells is known to be a major cause of Alzheimer's disease (for review, see Selkoe, 1998). The activity of presenilin therefore enhances the progression of Alzheimer's disease. This is supported by the observation that in the absence of presenilin gene, the production of alpha-beta42 peptide is lowered (De Strooper et al., Nature 391, 387 (1998)). Since unprocessed presenilin is degraded quickly, the processed, heterodimeric presenilin must be responsible for the accumulation of alpha-beta42 leading to Alzheimer's disease. The processing of presenilin by memapsin 2 would enhance the production of alpha-beta42 and therefore, further the progress of Alzheimer's disease. Therefore a memapsin 2 inhibitor that crosses the blood brain barrier can be used to decrease the likelihood of developing or slow the progression of Alzheimer's disease which is mediated by deposition of alpha-beta42. Since memapsin 2 cleaves APP at the beta cleavage site, prevention of APP cleavage at the beta cleavage site will prevent the build up of alpha-beta42.

Vaccines

The catalytically active memapsin 2 or fragments thereof including the active site defined by the presence of two catalytic aspartic residues and substrate binding cleft can be used to induce an immune response to the memapsin 2. The memapsin 2 is administered in an amount effective to elicit blocking antibodies, i.e., antibodies which prevent cleavage of the naturally occurring substrate of memapsin 2 in the brain. An unmodified vaccine may be useful in the prevention and treatment of Alzheimer's disease. The response to the vaccine may be influenced by its composition, such as inclusion of an adjuvant, viral proteins from production of the recombinant enzyme, and/or mode of administration (amount, site of administration, frequency of administration, etc). Since it is clear that the enzyme must be properly folded in order to be active, antibody should be elicited that is active against the endogenous memapsin 2. Antibodies that are effective against the endogenous enzyme are less likely to be produced against the enzyme that is not properly refolded.

Pharmaceutically Acceptable Carriers

The inhibitors will typically be administered orally or by injection. Oral administration is preferred. Alternatively, other formulations can be used for delivery by pulmonary, mucosal or transdermal routes. The inhibitor will usually be administered in combination with a pharmaceutically acceptable carrier. Pharmaceutical carriers are known to those skilled in the art. The appropriate carrier will typically be selected based on the mode of administration. Pharmaceutical compositions may also include one or more active ingredients such as antimicrobial agents, antiinflammatory agents, and analgesics.

Preparations for parenteral administration or administration by injection include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Preferred parenteral vehicles include sodium chloride solution, Ringer's dextrose, dextrose and sodium chloride, lactated Ringer's, or fixed oils. Intravenous vehicles include fluid and nutrient replenishers, and electrolyte replenishers (such as those based on Ringer's dextrose).

Formulations for topical (including application to a mucosal surface, including the mouth, pulmonary, nasal, vaginal or rectal) administration may include ointments, lotions, creams, gels, drops, suppositories, sprays, liquids and powders. Formulations for these applications are known. For example, a number of pulmonary formulations have been developed, typically using spray drying to formulate a powder having particles with an aerodynanmic diameter of between one and three microns, consisting of drug or drug in combination with polymer and/or surfactant.

Compositions for oral administration include powders or granules, suspensions or solutions in water or non-aqueous media, capsules, sachets, or tablets. Thickeners, flavorings, diluents, emulsifiers, dispersing aids or binders may be desirable.

Peptides as described herein can also be administered as a pharmaceutically acceptable acid- or base- addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Dosages

Dosing is dependent on severity and responsiveness of the condition to be treated, but will normally be one or more doses per day, with course of treatment lasting from several days to several months or until the attending physician determines no further benefit will be obtained. Persons of ordinary skill can determine optimum dosages, dosing methodologies and repetition rates.

The dosage ranges are those large enough to produce the desired effect in which the symptoms of the memapsin 2 mediated disorder are alleviated (typically characterized by a decrease in size and/or number of amyloid plaque, or by a failure to increase in size or quantity), or in which cleavage of the alpha-beta42 peptide is decreased. The dosage can be adjusted by the individual physician in the event of any counterindications.

The present invention will be further understood by reference to the following non-limiting examples.

EXAMPLE 1

Cloning of memapsin 2

1. Cloning and nucleotide sequence of pro-memapsin 2.

New sequences homologous to human aspartic proteases were found in the following entries in the EST IMAGE database: AA136368 pregnant uterus ATCC 947471, AA207232 neurepithelium ATCC 214526, and R55398 human breast ATCC 392689. The corresponding bacterial strains: #947471, #214526, and # 392689 containing the EST sequences were obtained from the ATCC (Rockville, Md.). The sequencing of these clones obtained from ATCC confirmed that they contained sequences not identical to known human aspartic proteases. The completed sequences of these clones assembled into about 80% of prepro-M2 cDNA. Full length cDNAs of these clones were obtained using the following methods.

The Human Pancreas Marathon-Ready cDNA (Clontech), which is double-strand cDNA obtained by reverse-transcription, primer addition, and second strand synthesize of mRNA from human tissues, was used as template for PCR amplification. An adapter primer (AP1) and a nested adapter primer (AP2) were used for 5'- and 3'-RACE PCR. For PCR the 5'-region of the memapsin 2 cDNA, primers AP1 and NHASPR1 were used. Primers for the 3'-end of the cDNA are NHASPF2 and AP 1. The middle of the cDNA was amplified by primers NHASPF1 and NHASPR2. The sequence for the primers is as follows:

NHASPF1: GGTAAGCATCCCCCATGGCCCCAACGTC (SEQ ID NO: 10),
NHASPR1: GACGTTGGGGCCATGGGGGATGCTTACC (SEQ ID NO: 11),
NHASPF2: ACGTTGTCTTTGATCGGGCCCGAAAAC-GAATTGG (SEQ ID NO: 12),
NHASPR2: CCAATTCGTTTTCGGGCCCGATCAAA-GACAACG (SEQ ID NO:13),
AP1: CCATCCTAATACGACTCACTATAGGGC (SEQ ID NO: 14), and
AP2: ACTCACTATAGGGCTCGAGCGGC (SEQ ID NO:15)

Memapsin 2 was also cloned from a human pancreas library (Quick-Screen Human cDNA Library Panel) contained in lambda-gt10 and lambda-gt11 vectors. The primers from the vectors, GT10FWD, GT10REV, GT11FWD, and GT11REV, were used as outside primers. The sequence of the primers used was:

GT10FWD: CTTTTGAGCAAGTTCAGCCTGGTTAA (SEQ ID NO:16),
GT10REV: GAGGTGGCTTATGAGTATTTCTTC-CAGGGTA (SEQ ID NO:17),
GT11FWD: TGGCGACGACTCCTGGAGCCCG (SEQ ID NO: 18),
GT11REV: TGACACCAGACCAACTGGTAATGG (SEQ ID NO:19).

In addition, memapsin 2 cDNA was amplified directly from the human pancreatic lambda-gt10 and lambda-gt11 libraries. The sequence of the primers was:

PASPN1: catatgGCGGGAGTGCTGCCTGCCCAC (SEQ ID NO:20) and
NHASPC1: ggatccTCACTTCAGCAGGGAGATGT-CATCAGCAAAGT (SEQ ID NO:21).

The amplified memapsin 2 fragments were cloned into an intermediate PCR vector (Invitrogen) and sequenced.

The assembled cDNA from the fragments, the nucleotide and the deduced protein sequence are shown in SEQ ID NO 1 and SEQ ID NO 2.

Pro-memapsin 2 is homologous to other human aspartic proteases. Based on the alignments, Pro-memapsin 2 contains a pro region, an aspartic protease region, and a trans-membrane region near the C-terminus. The active enzyme is memapsin 2 and its pro-enzyme is pro-memapsin 2.

EXAMPLE 2

Distribution of memapsin 2 in human tissues.

Multiple tissue cDNA panels from Clontech were used as templates for PCR amplification of a 0.82 kb fragment of memapsin 2 cDNA. The primers used for memapsin 2 were NHASPF1 and NHASPR2. Tissues that contain memapsin 2 or fragments of memapsin 2 yielded amplified PCR products. The amount of amplified product indicated that memapsin 2 is present in the following organs from most abundant to least abundant: pancreas, brain, lung, kidney, liver, placenta, and heart. Memapsin 2 is also present in spleen, prostate, testis, ovary, small intestine, and colon cells.

EXAMPLE 3

Expression of pro-memapsin 2 cDNA in E. coli, refolding and purification of pro-memapsin 2.

The pro-memapsin 2 was PCR amplified and cloned into the BamHil site of a pET11a vector. The resulting vector expresses pro-memapsin 2 having a sequence from Ala-8p to Ala 326. FIG. 1 shows the construction of two expression vectors, pET11-memapsin 2-T1 (hereafter T1) and pET11-memapsin 2-T2 (hereafter T2). In both vectors, the N-terminal 15 residues of the expressed recombinant proteins are derived from the expression vector. Pro-memapsin 2 residues start at residue Ala-16. The two recombinant pro-memapsin 2s have different C-terminal lengths. Clone T1 ends at Thr-454 and clone T2 ends at Ala-419. The T1 construct contains a C-terminal extension from the T2 construct but does not express any of the predicted trans-membrane domain.

Expression of recombinant proteins and recovery of inclusion bodies

The T1 and T2 expression vectors were separately transfected into E. coli strain BL21 (DE3). The procedures for the culture of transfected bacteria, induction for synthesis of recombinant proteins and the recovery and washing of inclusion bodies containing recombinant proteins are essentially as previously described (Lin et al., 1994).

Three different refolding methods have produced satisfactory results.

(i) The rapid dilution method.

Pro-memapsin 2 in 8M urea/100 mM beta-mercaptoethanol with $OD_{280nm}=5$ was rapidly diluted into 20 volumes of 20 mM-Tris, pH 9.0. The solution was slowly adjusted into pH 8 with 1M HCl. The refolding solution was then kept at 4° C. for 24 to 48 hours before proceeding with purification.

(ii) The reverse dialysis method

An equal volume of 20 mM Tris, 0.5 mM oxidized/1.25 mM reduced glutathione, pH 9.0 is added to rapidly stirred pro-memapsin 2 in 8M urea/10 mM beta-mercaptoethanol with $OD_{280nm}=5$. The process is repeated three more times with 1 hour intervals. The resulting solution is then dialyzed against sufficient volume of 20 mM Tris base so that the final urea concentration is 0.4M. The pH of the solution is then slowly adjusted to 8.0 with 1M HCl.

iii. The preferred method for refolding.

Inclusion bodies are dissolved in 8M urea, 0.1M Tris, 1 mM Glycine, 1 mM EDTA, 100 mM beta-mercaptoethanol, pH 10.0. The OD$_{280}$ of the inclusion bodies are adjusted to 5.0 with the 8 M urea solution without beta-mercaptoethanol. The final solution contains the following reducing reagents: 10 mM beta-mercaptoethanol, 10 mM DTT (Dithiothreitol), 1 mM reduced glutathion, and 0.1M oxidized glutathion. The final pH of the solution is 10.0.

The above solution is rapidly diluted into 20 volumes of 20 mM Tris base, the pH is adjusted to 9.0, and the resulting solution is kept at 4° C. for 16 hr. The solution is equilibrated to room temperature in 6 hr, and the pH is adjusted to 8.5. The solution is returned to 4° C. again for 18 hr.

The solution is again equilibrated to room temperature in 6 hr, and the pH is adjusted to 8.0. The solution is returned to 4° C. again for 4 to 7 days.

The refolding procedures are critical to obtain an enzymically active preparation which can be used for studies of subsite specificity of M2, to analyze inhibition potency of M2 inhibitors, to screen for inhibitors using either random structural libraries or existing collections of compound libraries, to produce crystals for crystallography studies of M2 structures, and to produce monoclonal or polyclonal antibodies of M2.

subjected to HPLC on a reversed phase C-18 column and the eluent peaks were subjected to electrospray mass spectrometry for the determination of the molecular weight of the fragments. Two hydrolytic sites were identified on oxidized insulin B-chain (Table 1). Three hydrolytic sites were identified from peptide NCH-gamma. A single cleavage site was observed in synthetic peptide PS1-gamma, whose sequence (LVNMAEGD) (SEQ ID NO:9) is derived from the beta-processing site of human presenilin 1 (Table 1).

TABLE 1

Substrate Specificity of Memapsin 2

| Site # | Substrate | P4 | P3 | P2 | P1 | P1' | P2' | P3' | P4' | |
|---|---|---|---|---|---|---|---|---|---|---|
| 1 | Pro- | R | G | S | M | A | G | V | L | aa 12–18 of SEQ ID No. 3 |
| 2 | memapsin 2 | G | T | Q | H | G | I | R | L | aa 23–30 of SEQ ID No. 3 |
| 3 |  | S | S | N | F | A | V | G | A | aa 98–105 of SEQ ID No. 3 |
| 4 |  | G | L | A | Y | A | E | I | A | aa 183–190 of SEQ ID No. 3 |
| 5 | Oxidized | H | L | C^ | G | S | H | L | V | C^ is cysteic acid; |
| 6 | insulin B-chain' | C^ | G | E | R | G | F | F | Y | SEQ ID No. 22 |
|  |  |  |  |  |  |  |  |  |  | SEQ ID No. 23 |
| 7 | Synthetic |  |  |  | V | G | S | G | V | Three sites cleaved in a peptide: |
| 8 | peptide* |  | V | G | S | G | V | L | L | VGSGVLLSRK (SEQ ID |
| 9 |  | G | V | L | L | S | R | K |  | NO: 30) |
|  |  |  |  |  |  |  |  |  |  | SEQ ID No. 24 |
|  |  |  |  |  |  |  |  |  |  | SEQ ID No. 25 |
|  |  |  |  |  |  |  |  |  |  | SEQ ID No. 26 |
| 10 | Peptide** | L | V | N | M | A | E | G | D | SEQ ID No. 9 |

EXAMPLE 4

Proteolytic activity and cleavage-site preferences of recombinant memapsin 2.

The amino acid sequence around the proteolytic cleavage sites was determined in order to establish the specificity of memapsin 2. Recombinant pro-memapsin 2-T1 was incubated in 0.1M sodium acetate, pH 4.0, for 16 hours at room temperature in order to create autocatalyzed cleavages. The products were analyzed using SDS-polyacrylamide gel electrophoresis. Several bands which corresponded to molecular weights smaller than that of pro-memapsin 2 were observed. The electrophoretic bands were trans-blotted onto a PVDF membrane. Four bands were chosen and subjected to N-terminal sequence determination in a Protein Sequencer. The N-terminal sequence of these bands established the positions of proteolytic cleavage sites on pro-memapsin 2.

In addition, the oxidized β-chain of bovine insulin and two different synthetic peptides were used as substrates for memapsin 2 to determine the extent of other hydrolysis sites. These reactions were carried out by auto-activated pro-memapsin 2 in 0.1M sodium acetate, pH 4.0, which was then incubated with the peptides. The hydrolytic products were

EXAMPLE 5

Activation of pro-memapsin 2 and enzyme kinetics.

Incubation in 0.1M sodium acetate, pH 4.0, for 16 h at 22° C. auto-catalytically converted pro-M2$_{pd}$ to M2$_{pd}$. For initial hydrolysis tests, two synthetic peptides were separately incubated with pro-M2$_{pd}$ in 0.1M Na acetate, pH 4.0 for different periods ranging from 2 to 18 h. The incubated samples were subjected to LC/MS for the identification of the hydrolytic products. For kinetic studies, the identified HPLC (Beckman System Gold) product peaks were integrated for quantitation. The K$_m$ and k$_{cat}$ values for presenilin 1 and Swedish APP peptides (Table 1) were measured by steady-state kinetics. The individual K$_m$ and K$_{cat}$ values for APP peptide could not be measured accurately by standard methods, so its k$_{cat}$/K$_m$ value was measured by competitive hydrolysis of mixed substrates against presenilin 1 peptide (Fersht, A. "Enzyme Structure and Mechanism", 2$^{nd}$ Ed., W. H. Freeman and Company, New York. (1985)).

Figure 2B:
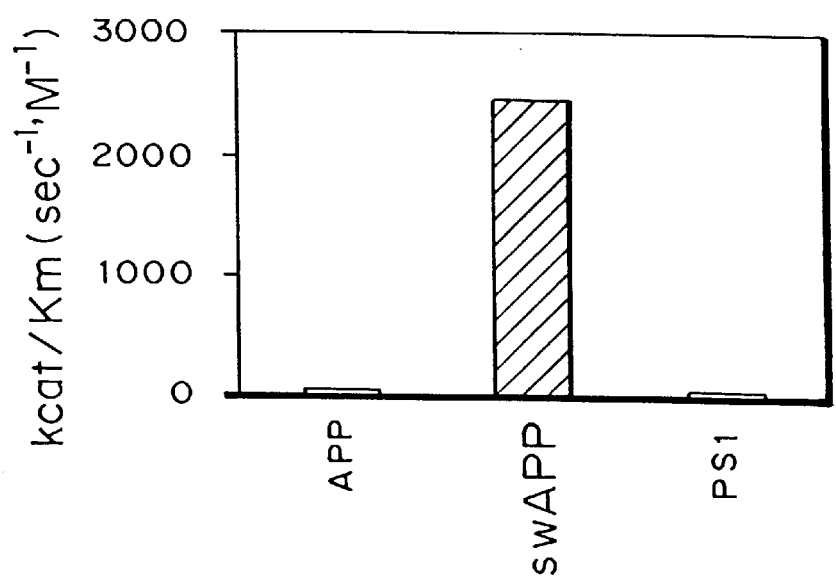
FIG. 2B is a graph of the relative $k_{cat}/K_m$ values for steady-state kinetic of hydrolysis of peptide substrates by $M2_{pd}$.

The results are shown in FIGS. 2A and 2B. The conversion of pro-M2$_{pd}$ at pH 4.0 to smaller fragments was shown by SDS-polyacrylamide electrophoresis. The difference in migration between pro-M2$_{pd}$ and converted enzyme is evident in a mixture of the two. FIG. 2A is a graph of the initial rate of hydrolysis of synthetic peptide swAPP (see Table 1) by M2$_{pd}$ at different pH. FIG. 2B is a graph of the relative k$_{cat}$/K$_m$ values for steady-state kinetic of hydrolysis of peptide substrates by M2$_{pd}$.

EXAMPLE 6

Expression in Mammalian cells.

Methods

PM2 cDNA was cloned into the EcoRV site of vector pSecTag A (Invitrogen). Human APP cDNA was PCR amplified from human placenta 8-gt11 library (Clontech)

and cloned into the NheI and XbaI sites of pSecTag A. The procedure for transfection into HeLa cells and vaccinia virus infection for T7-based expression are essentially the same as described by Lin, X., *FASEB J* 7:1070–1080 (1993).

Transfected cells were metabolically labeled with 200 microCi $^{35}$S methionine and cysteine (TransLabel; ICN) in 0.5 ml of serum-free/methionine-free media for 30 min, rinsed with 1 ml media, and replaced with 2 ml DMEM/10% FCS. In order to block vesicle acidification, Bafilomycin A1 was included in the media (Perez, R. G., et al., *J. Biol. Chem* 271:9100–9107 (1996)). At different time points (chase), media was removed and the cells were harvested and lysed in 50 mM Tris, 0.3M NaCl, 5 mM EDTA, 1% Triton X-100, pH 7.4, containing 10 mM iodoacetamide, 10:M TPCK, 10 :M TLCK, and 2 microg/ml leupeptin. The supernatant (14,000 xg) of cell lysates and media were immunoadsorbed onto antibody bound to protein G sepharose (Sigma). Anti-APP N-terminal domain antibody (Chemicon) was used to recover the betaN-fragment of APP and anti-alpha-beta 1–17 antibody (Chemicon, recognizing the N-terminal 17 residues of alpha-beta) was used to recover the 12 kDa βC-fragment. The former antibody recognized only denatured protein, so media was first incubated in 2 mM dithiothrietol 0.1% SDS at 55° C. for 30 min before immunoabsorption. Samples were cooled and diluted with an equal volume of cell lysis buffer before addition of anti-APP N-terminal domain (Chemicon). Beads were washed, eluted with loading buffer, subjected to SDS-PAGE (NOVEX™) and visualized by autoradiogram or phosphorimaging (Molecular Dynamics) on gels enhanced with Amplify (Amersham). Immunodetection of the betaN-fragment was accomplished by transblotting onto a PVDF membrane and detecting with anti-alpha-beta$_{1-17}$ and chemiluminescent substrate (Amersham).

Results.

HeLa cells transfected with APP or M2 in 4-well chamber slides were fixed with acetone for 10 min and permeabilized in 0.2% Triton X-100 in PBS for 6 min. For localizing M2, polyclonal goat anti-pro-M2$_{pd}$ antibodies were purified on DEAE-sepharose 6B and affinity purified against recombinant pro-M2$_{pd}$ immobilized on Affigel (BioRad). Purified anti-pro-M2$_{pd}$ antibodies were conjugated to Alexa568 (Molecular Probes) according to the manufacturer's protocol. Fixed cells were incubated overnight with a 1:100 dilution of antibody in PBS containing 0.1% BSA and washed 4 times with PBS. For APP, two antibodies were used. Antibody A β$_{1-17}$ (described above) and antibody Aβ$_{17-42}$, which recognizes the first 26 residues following the beta-secretase cleavage site (Chemicon). After 4 PBS washes, the cells were incubated overnight with an anti-mouse FITC conjugate at a dilution of 1:200. Cells were mounted in Prolong anti-fade reagent (Molecular Probes) and visualized on a Leica TCS confocal laser scanning microscope.

EXAMPLE 7

Design and Synthesis of OM99-1 and OM99-2.

Figure 3A:
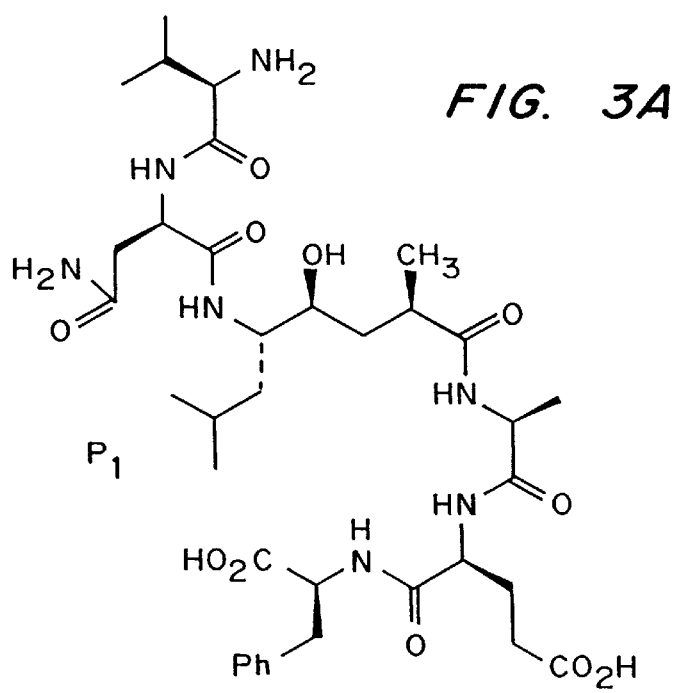
FIGS. 3A and 3B are the chemical structures of memapsin 2 inhibitors, OM99-2 and OM99-1.
Figure 3B:
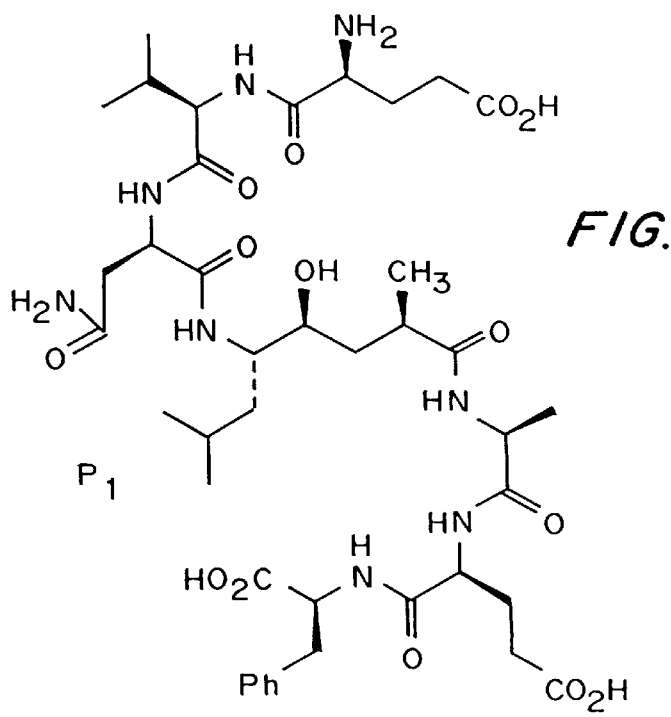

Based on the results of specificity studies of memapsin 2, it was predicted that good residues for positions P1 and P1' would be Leu and Ala. It was subsequently-determined from the specificity data that P1' preferred small residues, such as Ala and Ser. However, the crystal structure (determined below in Example 9) indicates that this site can accommodate a lot of larger residues. It was demonstrated that P1' of memapsin 2 is the position with the most stringent specificity requirement where residues of small side chains, such as Ala, Ser, and Asp, are preferred. Ala was selected for P1' mainly because its hydophobicity over Ser and Asp is favored for the penetration of the blood-brain barrier, a requirement for the design of a memapsin 2 inhibitor drug for treating Alzheimer's disease. Therefore, inhibitors were designed to place a transition-state analogue isostere between Leu and Ala (shown as Leu*Ala, where * represents the transition-state isostere, —CH(OH)—CH$_2$—) and the subsite P4, P3, P2, P2', P3' and P4' are filled with the beta-secretase site sequence of the Swedish mutant from the beta-amyloid protein. The structures of inhibitors OM99-1 and OM99-2 are shown below and in FIGS. 3A and 3B, respectively:

OM99-1: Val-Asn-Leu*Ala-Ala-Glu-Phe (SEQ. ID NO. 27)
OM99-2: Glu-Val-Asn-Leu*Ala-Ala-Glu-Phe (SEQ. ID NO.28)

The Leu*Ala dipeptide isostere was synthesized as follows:

The Leu-Ala dipeptide isostere for the M$_2$-inhibitor was prepared from L-leucine. As shown in Scheme 1, L-leucine was protected as its BOC-derivative 2 by treatment with BOC$_2$O in the presence of 10% NaOH in diethyl ether for 12 h. Boc-leucine 2 was then converted to Weinreb amide 3 by treatment with isobutyl chcloroformate and N-methylpiperidine followed by treatment of the resulting mixed anhydride with N,O-dimethylhydroxylamine

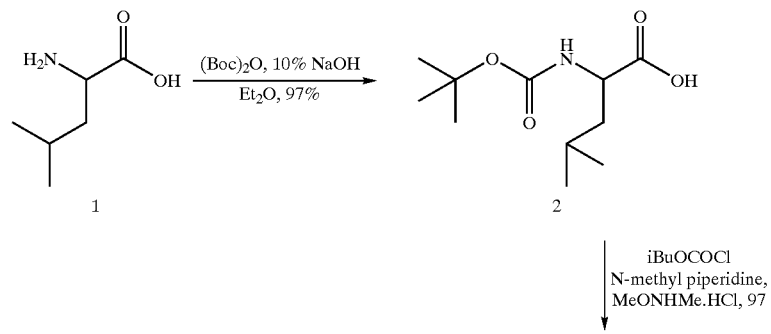

-continued

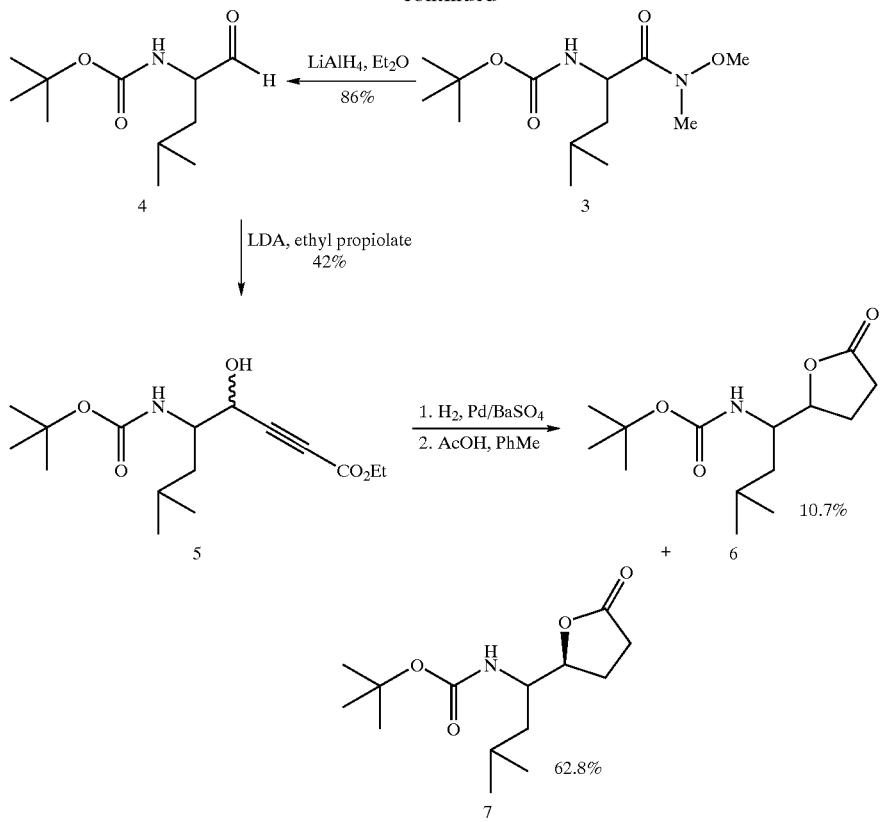

(Nahm and Weinreb, Tetrahedron Letters 1981, 32, 3815). Reduction of 3 with lithium aluminum hydride in diethyl ether provided the aldehyde 4. Reaction of the aldehyde 4 with lithium propiolate derived from the treatment of ethyl propiolate and lithium diisopropylamide afforded the acetylenic alcohol 5 as an inseparable mixture of diastereomers (5.8:1) in 42% isolated yield (Fray, Kaye and Kleinman, J. Org. Chem. 1986, 51, 4828–33). Catalytic hydrogenation of 5 over Pd/BaSO$_4$ followed by acid-catalyzed lactonization of the resulting gamma-hydroxy ester with a catalytic amount of acetic acid in toluene at reflux, furnished the gamma-lactone 6 and 7 in 73% yield. The isomers were separated by silica gel chromatography by using 40% ethyl acetate in hexane as the eluent.

(Scheme 2)

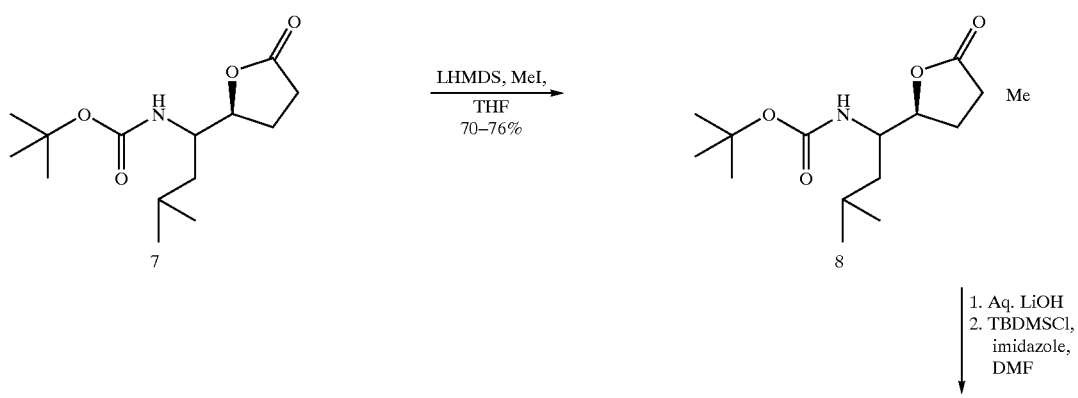

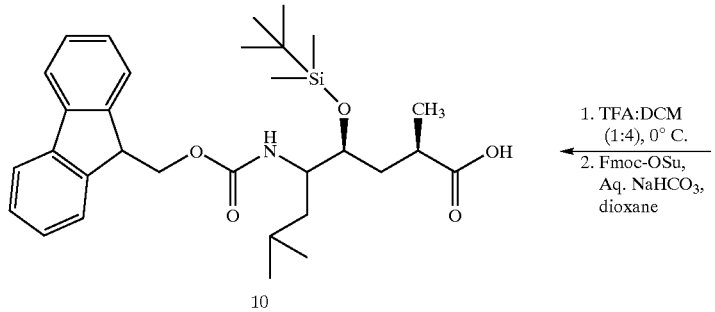 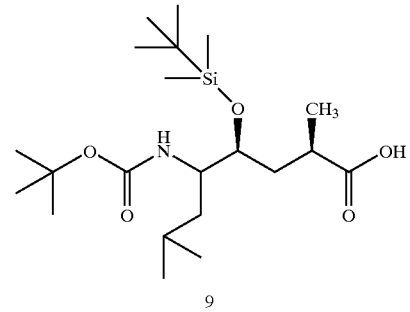

Introduction of the methyl group at C-2 was accomplished by stereoselective alkylation of 7 with methyl iodide (Scheme 2). Thus, generation of the dianion of lactone 7 with lithium hexamethyldisilazide (2.2 equivalents) in tetrahydrofuran at −78° C. (30 min) and alkylation with methyl iodide (1.1 equivalents) for 30 min at −78° C., followed by quenching with propionic acid (5 equivalents), provided the desired alkylated lactone 8 (76% yield) along with a small amount (less than 5%) of the corresponding epimer (Ghosh and Fidanze, 1998 J. Org. Chem. 1998, 63, 6146–54). The epimeric cis-lactone was removed by column chromatography over silica gel using a mixture (3:1) of ethyl acetate and hexane as the solvent system. The stereochemical assignment of alkylated lactone 8 was made based on extensive $^1$H-NMR NOE experiments. Aqueous lithium hydroxide promoted hydrolysis of the lactone 8 followed by protection of the gamma-hydroxyl group with tert-butyldimethylsilyl chloride in the presence of imidazole and dimethylaminopyridine in dimethylformamide afforded the acid 9 in 90% yield after standard work-up and chromatography. Selective removal of the BOC-group was effected by treatment with trifluoroacetic acid in dichloromethane at 0° C. for 1 h. The resulting amine salt was then reacted with commercial (Aldrich, Milwaukee) Fmoc-succinimide derivative in dioxane in the presence of aqueous NaHCO$_3$ to provide the Fmoc-protected L*A isostere 10 in 65% yield after chromatography. Protected isostere 10 was utilized in the preparation of a random sequence inhibitor library.

Experimental procedure

N-(tert-Butoxycarbonyl)-L-Leucine (2).

To the suspension of 10 g (76.2 mmol ) of L-leucine in 140 mL of diethyl ether was added 80 mL of 10% NaOH. After all solid dissolves, 20 mL (87.1 mmol) of BOC$_2$O was added to the reaction mixture. The resulting reaction mixture was stirred at 23° C. for 12 h. After this period, the layers were separated and the aqueous layer was acidified to pH 1 by careful addition of 1N aqueous HCl at 0° C. The resulting mixture was extracted with ethyl acetate (3×100 mL). The organic layers were combined and washed with brine and dried over anhydrous Na$_2$SO$_4$. The solvent was removed under reduced pressure to provide title product which was used directly for next reaction without further purification (yield, 97%). $^1$H NMR (400MHz, CDCl$_3$) δ 4.89 (broad d, 1H, J =8.3 Hz), 4.31 (m, 1H), 1.74–1.49 (m, 3H), 1.44 (s, 9H), 0.95 (d, 6H, J=6.5 Hz).

N-(tert-Butoxycarbonyl)-L-leucine-N'-methoxy-N'-methyla-mide (3).

To a stirred solution of N,O-dimethylhydroxyamine hydrochloride (5.52 g, 56.6 mmol) in dry dichloromethane (25 mL) under N$_2$ atmosphere at 0° C., —methylpiperidine (6.9 mL, 56.6 mmol) was added dropwise. The resulting mixture was stirred at 0° C. for 30 min. In a separate flask, N-(tert-butyloxycarbonyl)-L-leucine (1) (11.9 g, 51.4 mmol) was dissolved in a mixture of THF (45 mL) and dichloromethane (180 mL) under N$_2$ atmosphere. The resulting solution was cooled to −20° C. To this solution was added 1-methylpiperidine (6.9 mL, 56.6 mmol) followed by isobutyl chloroformate (7.3 mL, 56.6 mmol). The resulting mixture was stirred for 5 minutes at −20° C. and the above solution of N,O-dimethylhydroxyamine was added to it. The reaction mixture was kept −20° C. for 30 minutes and then warmed to 23° C. The reaction was quenched with water and the layers were seperated. The aqueous layer was extracted with dichloromethane (3×100 mL). The combined organic layers were washed with 10% citric acid, saturated sodium bicarbonate, and brine. The organic layer was dried over anhydrous Na$_2$SO$_4$ and concentrated under the reduced pressure. The residue was purified by flash silica gel chromatography (25% ethyl acetate/hexane) to yield the title compound 3 (13.8 g, 97%) as a pale yellow oil. $^1$H NMR (400 MHz, CDCl$_3$) δ 5.06 (broad d, 1H, J=9.1 Hz), 4.70 (m, 1H), 3.82 (s, 3H), 3.13 (s, 3H), 1.70 (m, 1H), 1.46–1.36 (m, 2H) 1.41 (s, 9H), 0.93 (dd, 6H, J=6.5, 14.2 Hz).

N-(tert-Butoxycarbonyl)-L-leucinal (4).

To a stirred suspension of lithium aluminum hydride (770 mg, 20.3 mmol) in dry diethyl ether (60 mL) at −40° C. under N$_2$ atmosphere, was added N-tert-butyloxycarbonyl-L-leucine-N'-methoxy-N'-methylamide (5.05 g, 18.4 mmol) in diethyl ether (20 mL). The resulting reaction mixture was stirred for 30 min. After this period, the reaction was quenched with 10% NaHSO$_4$ solution (30 mL). The resulting reaction mixture was then warmed to 23° C. and stirred at that temperature for 30 min. The resulting solution was filtered and the filter cake was washed by two portions of diethyl ether. The combined organic layers were washed with saturated sodium bicarbonate, brine and dried over anhydrous MgSO$_4$. Evaporation of the solvent under reduced pressure afforded the title aldehyde 4 (3.41 g) as a pale yellow oil. The resulting aldehyde was used immediately without further purification. $^1$H NMR (400MHz, CDCl$_3$) δ 9.5 (s, 1H), 4.9 (s, 1H), 4.2 (broad m, 1H), 1.8–1.6 (m, 2H), 1.44 (s, 9H), 1.49–1.39 (m, 1H), 0.96 (dd, 6H, J=2.7, 6.5 Hz).

Ethyl (4S, 5S) -and (4R, 5S)-5-[(tert-Butoxycarbonyl) amino]-4-hydroxy-7-methyloct-2-ynoate (5).

To a stirred solution of diisopropylamine (1.1 mL, 7.9 mmol) in dry THF (60 mL) at 0° C. under N$_2$ atmosphere, was added n-BuLi (1.6M in hexane, 4.95 mL, 7.9 mmol) dropwise. The resulting solution was stirred at 0° C. for 5 min and then warmed to 23° C. and stirred for 15 min. The mixture was cooled to −78° C. and ethyl propiolate (801 μL) in THF (2 mL) was added dropwise over a period of 5 min. The mixture was stirred for 30 min, after which N-Boc-L-leucinal 4 (1.55 g, 7.2 mmol) in 8 mL of dry THF was added.

The resulting mixture was stirred at −78° C. for 1 h. After this period, the reaction was quenched with acetic acid (5 mL) in THF (20 mL). The reaction mixure was warmed up to 23° C. and brine solution was added. The layers were separated and the organic layer was washed with saturated sodium bicarbonate and dried over $Na_2SO_4$. Evaporation of the solvent under reduced pressure provided a residue which was purified by flash silica gel chromatography (15% ethyl acetate/hexane) to afford a mixture (3:1) of acetylenic alcohols 5 (0.96 g, 42%). $^1$H NMR (300MHz, $CDCl_3$) δ 4.64 (d, 1H, J=9.0 Hz), 4.44 (broad s, 1H), 4.18 (m, 2H), 3.76 (m, 1H), 1.63 (m, 1H), 1.43–1.31 (m, 2H), 1.39 (s, 9H), 1.29–1.18 (m, 3H), 0.89 (m, 6H).

(5S,1'S)-5-[1'-[(tert-Butoxycarbonyl)amino]-3'-methylbutyl]-dihydrofuran-2(3H)-one (7).

To a stirred solution of the above mixture of acetylenic alcohols (1.73 g, 5.5 mmol) in ethyl acetate (20 mL) was added 5% $Pd/BaSO_4$ (1 g). The resulting mixture was hydrogenated at 50 psi for 1.5 h. After this period, the catalyst was filtered off through a plug of Celite and the filtrate was concentrated under reduced pressure. The residue was dissolved in toluene (20 mL) and acetic acid (100 μL). The reaction mixture was refluxed for 6 h. After this period, the reaction was cooled to 23° C. and the solvent was evaporated to give a residue which was purified by flash silica gel chromatography (40% diethyl ether/hexane) to yield the (5S,1S')-gamma-lactone 7 (0.94 g, 62.8 and the (5R,1S')-gamma-lactone 6 (0.16 g, 10.7%). Lactone 7: $^1$H NMR (400 MHz, $CDCl_3$) δ 4.50–4.44 (m, 2H), 3.84–3.82 (m, 1H), 2.50 (t, 2H, J=7.8 Hz), 2.22–2.10 (m, 2H), 1.64–1.31 (m, 3H), 1.41 (s, 9H), 0.91 (dd, 6H, J=2.2, 6.7 Hz); $^{13}$C NMR (75MHz, $CDCl_3$) δ 177.2, 156.0, 82.5, 79.8, 51.0, 42.2, 28,6, 28.2, 24.7, 24.2, 23.0, 21.9.

(3R, 5S,1'S)-5-[1'-[(tert-Butoxycarbonyl)amino]-3'-methylbut-yl]-3-methyl dihydrofuran-2(3H)-one (8).

To a stirred solution of the lactone 7 (451.8 mg, 1.67 mmol) in dry THF (8 mL) at −78° C. under $N_2$ atmosphere, was added lithium hexamethyldisilazane (3.67 mL, 1.0M in THF) over a period of 3 min. The resulting mixture was stirred at −78° C. for 30 min to generate the lithium enolate. After this period, MeI (228 μL) was added dropwise and the resulting mixture was stirred at −78° C. for 20 min. The reaction was quenched with saturated aqueous $NH_4Cl$ solution and was allowed to warm to 23° C. The reaction mixture was concentrated under reduced pressure and the residue was extracted with ethyl acetate (3×100 mL). The combined organic layers were washed with brine and dried over anhydrous $Na_2SO_4$. Evaporation of the solvent afforded a residue which was purified by silica gel chromatography (15% ethyl acetate/hexane) to furnish the alkylated lactone 8 (0.36 g, 76%) as an amorphous solid. $^1$H NMR (300MHz, $CDCl_3$) δ 4.43 (broad t, 1H, J=6.3 Hz), 4.33 (d, 1H, J=9.6 Hz), 3.78 (m, 1H), 2.62 (m, 1H), 2.35 (m, 1H), 1.86 (m, 1H), 1.63–1.24 (m, 3H), 1.37 (s, 9H), 1.21 (d, 3H, J=7.5 Hz), 0.87 (dd, 6H, J=2.6, 6.7 Hz); $^{13}$C NMR (75MHz, $CDCl_3$) δ 180.4, 156.0, 80.3, 79.8, 51.6, 41.9, 34.3, 32.5, 28.3, 24.7, 23.0, 21.8, 16.6.

(2R,4S,5S)-5-[(tert-Butoxycarbonyl)amino]-4-[(tert-butyldimeth-ylsilyl)oxy]-2,7-dimethyloctanoic acid (9).

To a stirred solution of lactone 8 (0.33 g, 1.17 mmol ) in THF (2 mL) was added 1N aqueous LiOH solution (5.8 mL). The resulting mixture was stirred at 23° C. for 10 h. After this period, the reaction mixture was concentrated under reduced pressure and the remaining aqueous residue was cooled to 0° C. and acidified with 25% citric acid solution to pH 4. The resulting acidic solution was extracted with ethyl acetate (3×50 mL). The combined organic layers were washed with brine, dried over $Na_2SO_4$ and concentrated to yield the corresponding hydroxy acid (330 mg) as a white foam. This hydroxy acid was used directly for the next reaction without further purification.

To the above hydroxy acid (330 mg, 1.1 mmol) in anhydrous DMF was added imidazole (1.59 g, 23.34 mmol) and tert-butyldimethylchlorosilane (1.76 g, 11.67 mmol). The resulting mixture was stirred at 23° C. for 24 h. After this period, MeOH (4 mL) was added and the mixture was stirred for 1 h. The mixture was diluted with 25% citric acid (20 mL) and was extracted with ethyl acetate (3×20 mL). The combined extracts were washed with water, brine and dried over anhydrous $Na_2SO_4$. Evaporation of the solvent gave a viscous oil which was purified by flash chromatography over silica gel (35% ethyl acetate/hexane) to afford the silyl protected acid 9 (0.44 g, 90%). IR (neat) 3300–3000 (broad), 2955, 2932, 2859, 1711 $cm^{-1}$; $^1$H NMR (400MHz, DMSO-$d^6$, 343 K) delta 6.20 (broad s, 1 H), 3.68 (m, 1H), 3.51 (broad s, 1H), 2.49–2.42 (m, 1H), 1.83 (t, 1H, J=10.1 Hz), 1.56 (m, 1H), 1.37 (s, 9H), 1.28–1.12 (m, 3H), 1.08 (d, 3H, J 7.1 Hz), 0.87 (d, 3H, J=6.1 Hz) 0.86 (s, 9 H), 0.82 (d, 3H, J=6.5 Hz), 0.084 (s, 3H), 0.052 (s, 3H).

(2R, 4S, 5S)-5-[(fluorenylmethyloxycarbonyl)amino]-4-[(tert-butyldi-methyl silyl)oxy]-2, 7-dimethyloctanoic acid (10).

To a stirred solution of the acid 9 (0.17 g , 0.41 mmol) in dichloromethane (2 mL) at 0° C. was added trifluoroacetic acid (500 μL). The resulting mixture was stirred at 0° C. for 1 h and an additional portion (500 μL) of trifluoroacetic acid was added to the reaction mixture. The mixture was stirred for an additional 30 min and the progress of the reaction was monitored by TLC. After this period, the solvents were carefully removed under reduced pressure at a bath temperature not exceeding 5° C. The residue was dissolved in dioxane (3 mL) and $NaHCO_3$ (300 mg) in 5 mL of $H_2O$. To this solution was added Fmoc-succinimide (166.5 mg, 0.49 mmol) in 5 mL of dioxane. The resulting mixture was stirred at 23° C. for 8 h. The mixture was then diluted with $H_2O$ (5 mL) and acidified with 25% aqueous citric acid to pH 4. The acidic solution was extracted with ethyl acetate (3×50 mL). The combined extracts were washed with brine, dried over $Na_2SO_4$ and concentrated under reduced pressure to give a viscous oil residue. Purification of the residue by flash chromatography over silica gel afforded the Fmoc-protected acid 10 (137 mg, 61%) as a white foam. $^1$H NMR (400MHz, DMSO-$d^6$, 343 K) δ 7.84 (d, 2H, J =7.4 Hz), 7.66 (d, 2H, J=8 Hz), 7.39 (t, 2H, J=7.4 Hz), 7.29 (m, 2H), 6.8 (s, 1H), 4.29–4.19 (m, 3H), 3.74–3.59 (m, 2H), 2.49 (m, 1H), 1.88 (m, 1H), 1.58 (m, 1H), 1.31–1.17 (m, 3H), 1.10 (d, 3H, J=7.1 Hz), 0.88 (s, 9H), 0.82 (d, 6H, J=6.2 Hz), 0.089 (s, 3 H), 0.057 (s, 3H).

The synthesis of OM99-1 and OM99-2 were accomplished using solid state peptide synthesis procedure in which Leu*Ala was incorporated in the fourth step. The synthesized inhibitors were purified by reverse phase HPLC and their structure confirmed by mass spectrometry.

EXAMPLE 8

Inhibition of Memapsin 2 by OM99-1 and OM99-2.

Figure 4A:
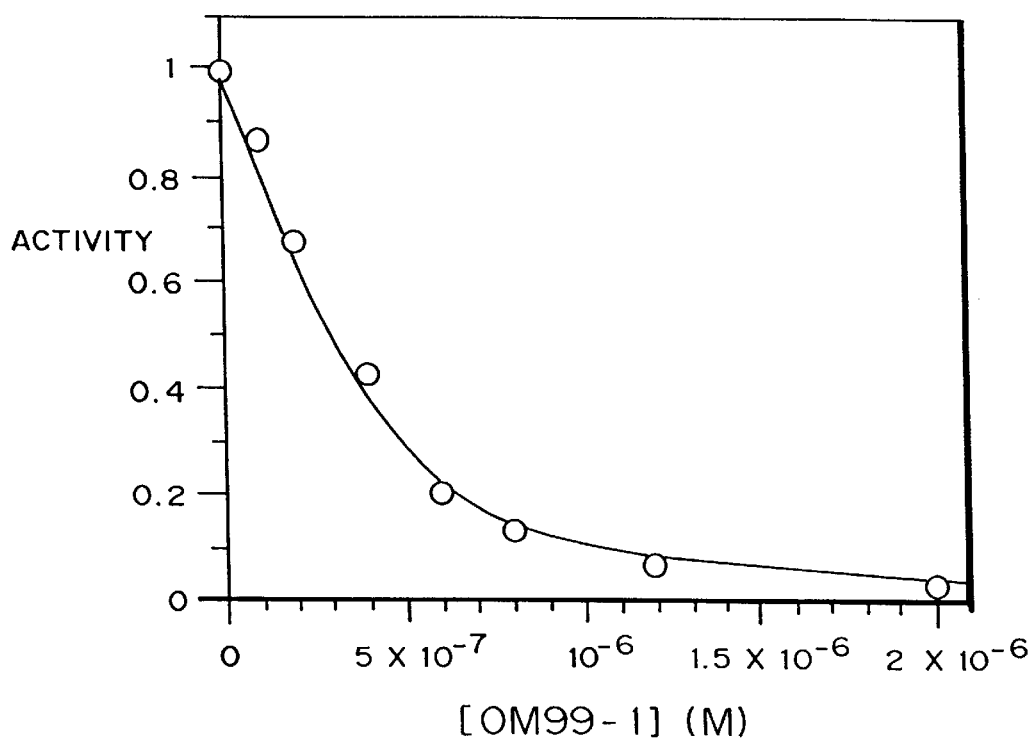
FIG. 4A is a graph of the inhibition of recombinant memapsin 2 by OM99-1.
Figure 4B:
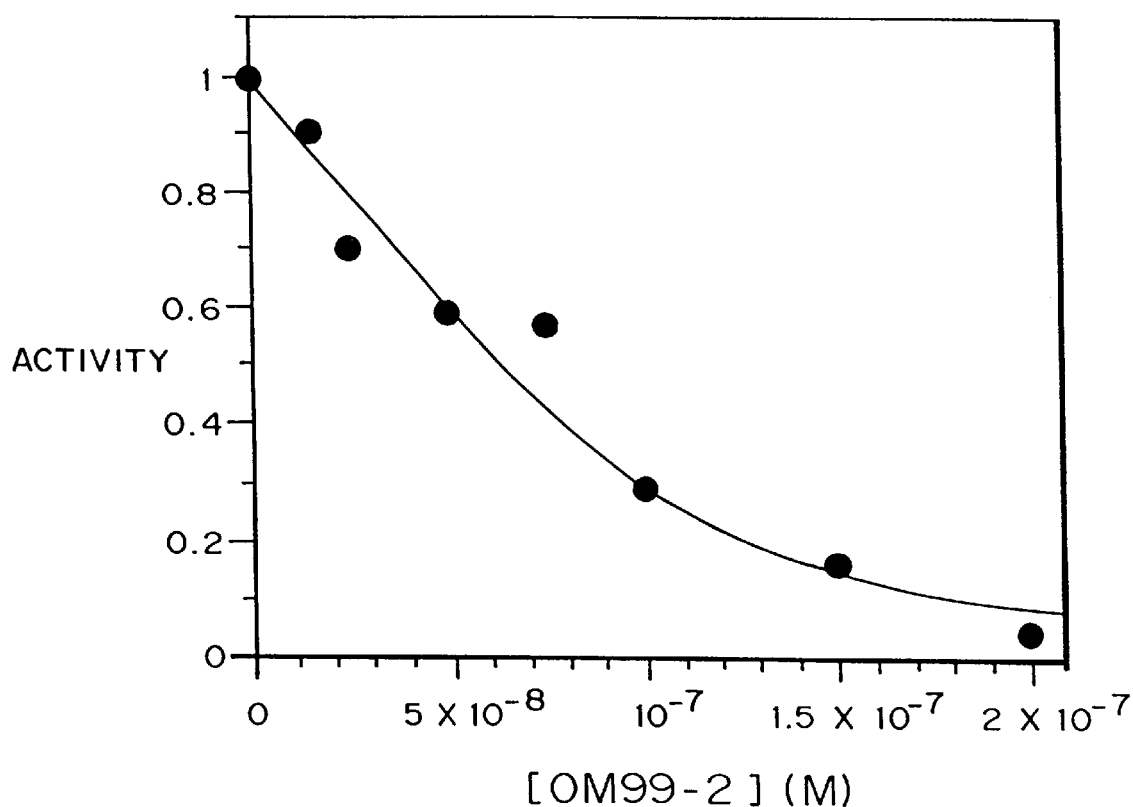
FIG. 4B is a graph of the inhibition of recombinant memapsin 2 by OM99-2.

Enzyme activity was measured as described above, but with the addition of either OM99-1 or OM99-2. OM99-1 inhibited recombinant memapsin 2 as shown in FIG. 4A. The Ki calculated is $3\times10^{-8}M$. The substrate used was a synthetic fluorogenic peptide substrate. The inhibition of OM99-2 on recombinant memapsin 2 was measured using the same fluorogenic substrate. The Ki value was determined to be 9.58×10$^{-9}$M, as shown in FIG. 4B.

These results demonstrate that the predicted subsite specificity is accurate and that inhibitors can be designed based on the predicted specificity.

The residues in P1 and P1' are very important since the M2 inhibitor must penetrate the blood-brain barrier (BBB). The choice of Ala in P1' facilitates the penetration of BBB. Analogues of Ala side chains will also work. For example, in addition to the methyl side chain of Ala, substituted methyl groups and groups about the same size like methyl or ethyl groups can be substituted for the Ala side chain. Leu at P1 can also be substituted by groups of similar sizes or with substitutions on Leu side chain. For penetrating the BBB, it is desirable to make the inhibitors smaller. One can therefore use OM99-1 as a starting point and discard the outside subsites P4, P3, P3' and P4'. The retained structure Asn-Leu*Ala-Ala (SEQ ID NO:29) is then further evolved with substitutions for a tight-binding M2 inhibitor which can also penetrate the BBB.

EXAMPLE 9

Crystallization and X-ray diffraction study of the protease domain of human memapsin 2 complexed to a specifically designed inhibitor, OM99-2.

The crystallization condition and preliminary x-ray diffraction data on recombinant human memapsin 2 complexed to OM99-2 were determined.

Production of Recombinant Memapsin 2

About 50 mg of recombinant memapsin 2 was purified as described in Example 3. For optimal crystal growth, memapsin 2 must be highly purified. Memapsin 2 was over-expressed from vector pET11a-$M2_{pd}$. This memapsin 2 is the zymogen domain which includes the pro and catalytic domains to the end of the C-terminal extension but does not include the transmembrane and the intracellular domains. The vector was transfected into *E. coli* BL21 (DE3) and plated onto ZB agar containing 50 mg/liter ampicillin. A single colony was picked to inoculate 100 ml of liquid ZB containing 5 mg ampicillin and cultured at 30° C., for 18 hours, with shaking at 220 RPM. Aliquots of approximately 15 ml of the overnight culture were used to inoculate each 1 liter of LB containing 50 mg of ampicillin. Cultures were grown at 37° C., with shaking at 180 RPM, until an optical density at 600 nm near 0.8 was attained. At that time, expression was induced by addition of 119 mg of IPTG to each liter of culture. Incubation was continued for 3 additional hours post-induction.

Bacteria were harvested, suspended in 50 mM Tris, 150 mM NaCl, pH 7.5 (TN buffer), and lysed by incubation with 6 mg lysozyme for 30 minutes, followed by freezing for 18 hours at −20° C. Lysate was thawed and made to 1 mM $MgCl_2$ then 1000 Kunitz units of DNAse were added with stirring, and incubated for 30 min. Volume was expanded to 500 ml with TN containing 0.1% Triton X-100 (TNT buffer) and lysate stirred for 30 minutes. Insoluble inclusion bodies containing greater than 90% memapsin 2 protein were pelleted by centrifugation, and washed by resuspension in TNT with stirring for 1–2 hours. Following three additional TNT washes, the memapsin 2 inclusion bodies were dissolved in 40 ml of 8M urea, 1 mM EDTA, 1 mM glycine, 100 mM Tris base, 100 mM beta-mercaptoethanlol (8M urea buffer). Optical density at 280 nm was measured, and volume expanded with 8M urea buffer to achieve final O.D. near 0.5, with addition of sufficient quantity of beta-mercaptoethanol to attain 10 mM total, and 10 mM DTT, 1 mM reduced glutathione, 0.1 mM oxidized glutathione. The pH of the solution was adjusted to 10.0 or greater, and divided into four aliquots of 200 ml each. Each 200 ml was rapidly-diluted into 4 liters of 20 mM Tris base, with rapid stirring. The pH was adjusted immediately to 9.0, with 1M HCl, and stored at 4° C. overnight. The following morning the diluted memapsin 2 solution was maintained at room temperature for 4–6 hours followed by adjusting pH to 8.5 and replacing the flasks to the 4° C. room. The same procedure was followed the next day with adjustment of pH to 8.0.

This memapsin 2 solution was allowed to stand at 4° C. for 2–3 weeks. The total volume of approximately 16 liters was concentrated to 40 mls using ultra-filtration (Millipore) and stir-cells (Amicon), and centrifuged at 140,000 xg at 30 minutes in a rotor pre-equilbrated to 4° C. The recovered supernatant was applied to a 2.5×100 cm column of S-300 equilibrated in 0.4M urea, 20 mM Tris-HCl, pH 8.0, and eluted with the same buffer at 30 ml/hour. The active fraction of memapsin 2 was pooled and further purified in a FPLC using a 1 ml Resource-Q (Pharmacia) column. Sample was filtered, and applied to the Resource-Q column equilibrated in 0.4M urea, 50 mM Tris-HCI, pH 8.0. Sample was eluted with a gradient of 0–1M NaCl in the same buffer, over 30 ml at 2 ml/min. The eluents containing memapsin 2 appeared near 0.4M NaCl which was pooled for crystallization procedure at a concentration near 5 mg/ml.

The amino-terminal sequence of the protein before crystallization showed two sequences starting respectively at residues 28 p and 30 p. Apparently, the pro peptide of recombinant pro-memapsin 2 had been cleaved during the preparation by a yet unidentified proteolytic activity.

The activation of the folded pro-enzyme to mature enzyme, memapsin 2, was carried out as described above, i.e., incubation in 0.1M sodium acetate pH 4.0 for 16 hours at 22° C. Activated enzyme was further purified using anion-exchange column chromatography on Resource-Q anion exchange column. The purity of the enzyme was demonstrated by SDS-gel electrophoresis. At each step of the purification, the specific activity of the enzyme was assayed as described above to ensure the activity of the enzyme.

Preliminary Crystallization with OM99-2

Crystal trials were performed on purified memapsin 2 in complex with a substrate based transition-state inhibitor OM99-2 with a Ki=10 nM. OM99-2 is equivalent to eight amino-acid residues (including subsites S4, S3, S2, S1 S1', S2', S3' and S4' in a sequence EVNLAAEF) with the substitution of the peptide bond between the S1 and S1' (L-A) by a transition-state isostere hydroxyethylene. Purified M2 was concentrated and mixed with 10 fold excessive molar amount of inhibitor. The mixture was incubated at room temperature for 2–3 hours to optimize the inhibitor binding. The crystallization trial was conducted at 20° C. using the hanging drop vapor diffusion procedure. A systemic search with various crystallization conditions was conducted to find the optimum crystallization conditions for memapsin 2/OM99-2 inhibitor complex. For the first step, a coarse screen aimed at covering a wide range of potential conditions were carried out using the Sparse Matrix Crystallization Screen Kits purchased from Hampton Research. Protein concentration and temperature were used as additional variables. Conditions giving promising (micro) crystals were subsequently used as starting points for optimization, using fine grids of pH, precipitants concentration etc.

Crystals of memapsin-inhibitor complex were obtained at 30% PEG 8000, 0.1M NaCocadylate, pH 6.4. SDS gel electrophoresis of a dissolved crystal verified that the content of the crystal to be memapsin 2. Several single crystals (with the sizes about 0.3 mm×0.2 mm×0.1 mm) were carefully removed from the cluster for data collection on a Raxis IV image plate. These results showed that the crystals diffract to 2.6 Å. An X-ray image visualization and integration software-Denzo, was used to visualize and index the diffraction data. Denzo identified that the primitive orthorhombic lattice has the highest symmetry with a significantly low distortion index. The unit cell parameters were determined as: a=89.1 Å, b=96.6 Å, c=134.1 Å, $\alpha=\beta=\gamma=90°$. There are two memapsin 2/OM99-2 complexes per crystallographic asymmetric unit, the Vm of the crystal is 2.9 Å$^3$/Da. Diffraction extinctions suggested that the space group is $P2_1 2_1 2_1$.

With diffraction of the current crystal to 2.6 Å, the crystal structure obtained from these data has the potential to reach atomic solution, i.e., the three-dimensional positions of atoms and chemical bonds in the inhibitor and in memapsin 2 can be deduced. Since memapsin 2 sequence is homologous with other mammalian aspartic proteases, e.g., pepsin or cathepsin D, it is predicted that the three dimensional structures of memapsin 2 will be similar (but not identical) to their structures. Therefore, in the determination of x-ray structure from the diffraction data obtained from the current crystal, it is likely the solution of the phase can be obtained from the molecular replacement method using the known crystal structure of aspartic proteases as the search model.

Further Crystallization Studies

Concentrated memapsin 2 was mixed with 10-fold molar excessive of the inhibitor. The mixture was incubated at room temperature for 2–3 hours to optimize inhibitor binding, and then clarified with a 0.2 micron filter using centrifugation. Crystals of memapsin 2-inhibitor complex were grown at 20° C. by hanging drop vapor diffusion method using equal volumes of enzyme-inhibitor and well solution. Crystals of quality suitable for diffraction studies were obtained in two weeks in 0.1M sodium cacodylate, pH 7.4, 0.2M $(NH_4)_2SO_4$, and 22.5% PEG8000. The typical size of the crystals was about 0.4×0.4×0.2 mm$^3$.

Diffraction data were measured on a Raxis-IV image plate with a Rigaku X-ray generator, processed with the HKL program package [Z. Otwinowski, W. Minor, Methods Enzymol. 276, 307 (1997)] A single crystal of approximately 0.4×0.4×0.2 mm$^3$ in size was treated with a cryo-protection solution of 25% PEG8000, 20% glycerol, 0.1M sodium-cacodylate pH 6.6, and 0.2M $(NH_4)_2SO_4$, and then flash-cooled with liquid nitrogen to about −180° C. for data collection. Diffraction was observed to at least 1.9 Å. The crystal form belongs to space group $P2_1$ with two memapsin 2/OM99-2 complexes per crystallographic asymmetric unit and 56% solvent content.

Molecular replacement was performed with data in the range of 15.0–3.5 Å using program AmoRe, CCP4 package [Navaza, J., Acta Crystallog. Sect. A. 50, 157 (1994)]. Pepsin, a human aspartic protease with 22% sequence identity, was used as the search model(PDB id 1psn). Rotation and translation search, followed by rigid body refinement, identified a top solution and positioned both molecules in the asymmetric unit. The initial solution had a correlation coefficient of 22% and an R-factor of 0.51. The refinement was carried out using the program CNS [Brunger et al., Acta Crystallog. Sect. D, 54, 905 (1998)]. 10% of reflections were randomly selected prior to refinement for $R_{free}$ monitoring [Bruger, A. T., X-PLOR Version 3.1: A system for X-ray Crystallography and NMR, Yale University Press, New Haven, Conn. (1992)]. Molecular graphics program [Jones, T. A., et al., Improved methods for building protein models in electron denisty maps and location of errors in these models. Acta Crystallogr. Sect. A 47, 110 (1991)] was used for map display and model building. From the initial pepsin model, corresponding amino acid residues were changed to that of memapsin 2 according to sequence alignment. The side chain conformations were decided by the initial electron density map and a rotomer library. This model was refined using molecular dynamics and energy minimization function of CNS [Bruger, A. T., et al., Acta Crystallogr. Sect. D, 54, 905 (1998)]. The first cycle of refinement dropped the $R_{working}$ to 41% and the $R_{free}$ to 45%. At this stage, electron densities in the omit map clearly showed the inhibitor configuration in the active site cleft. Structural features unique to memapsin 2 in chain tracing, secondary structure, insertions, deletions and extensions (as compared to the search model) are identified and constructed in subsequent iterations of crystallographic refinement and map fitting. The inhibitor was built into the corresponding electron density.

About 440 solvent molecules were then gradually added to the structure as identified in the $|F_o|-|F_c|$ map contoured at the 3 sigma level. Non-crystallographic symmetry restriction and averaging were used in early stages of refinement and model building. Bulk solvent and anisotropic over-all B factor corrections were applied through the refinement. The final structure was validated by the program PROCHECK Laskowski, R. A. et al., J. Appl. Crystallog. 26, 283 (1993) which showed that 95% of the residues are located in the most favored region of the Ramachandran plot. All the main chain and side chain parameters are within or better than the standard criteria. The final $R_{working}$ and $R_{free}$ are 18% and 22% respectively. Refinement statistics are listed in Table 2.

TABLE 2

Data Collection and Refinement Statistics

| A. Data Statistics | |
|---|---|
| Space group | $P2_1$ |
| Unit Cell (a, b, c, in Å) | 53.7, 85.9, 109.2 |
| ($\alpha$, $\beta$, $\gamma$ in degrees) | 90.0, 101.4, 90.0 |
| Resolution (Å) | 25.0–1.9 |
| Number of observed reflections | 144, 164 |
| Number of unique reflections | 69, 056 |
| $R_{merge}$[a] | 0.061 (0.25) |
| Data completeness (%) (25.0–1.9Å) | 90.0 (68.5) |
| <I/$\sigma$(I)> | 13.7 (3.0) |
| B. Refinement Statistics | |
| $R_{working}$[b] | 0.186 |
| $R_{free}$[b] | 0.228 |
| RMS deviation from ideal values | |
| Bond length (Å) | 0.014 |
| Bond angle (Deg) | 1.7 |
| Number of water molecules | 445 |
| Average B-factor (Å$^2$) | |
| Protein | 28.5 |
| Solvent | 32.2 |

[a]$R_{merge} = \Sigma_{hkl} \Sigma_i | I_{hkl, i} - <I_{hkl}> | / \Sigma_{hkl} <I_{hkl}>$, where $I_{hkl, i}$ is the intensity of the ith measurement and $<I_{hkl}>$ is the weighted mean of all measurements of $I_{hkl}$.
[b]$R_{working \, (free)} = \Sigma|F_o| - |F_c| / \Sigma|F_o|$, where $F_o$ and $F_c$ are the observed and calculated structure factors. Numbers in parentheses are the corresponding numbers for the highest resolution shell (2.00–1.9Å). Reflections with $F_o/\sigma$ ($F_o$) $\geq$ 0.0 are included in the refinement and R factor calculation.

Memapsin 2 Crystal Structure.

The bilobal structure of memapsin 2 (FIG. 6) is characteristic of aspartic proteases (Tang, J., et al., Nature 271, 618–621 (1978)) with the conserved folding of the globular core. The substrate binding cleft, where the inhibitor is bound (FIG. 6), is located between the two lobes. A pseudo two-fold symmetry between the N- (residues 1 - 180) and C- (residues 181–385) lobes (FIG. 6), which share 61 superimposable atoms with an overall 2.3 Å rms deviation using a 4 Å cutoff. The corresponding numbers for pepsin are 67 atoms and 2.2 Å. Active-site $Asp^{32}$ and $ASp^{228}$ and the surrounding hydrogen-bond network are located in the center of the cleft (FIG. 6) and are conserved with the typical active-site conformation (Davies, D. R., Annu. Rev. Biophys. Chem. 19, 189 (1990)). The active site carboxyls are, however, not co-planar and the degree of which (50°) exceeds those observed previously.

Figure 6:
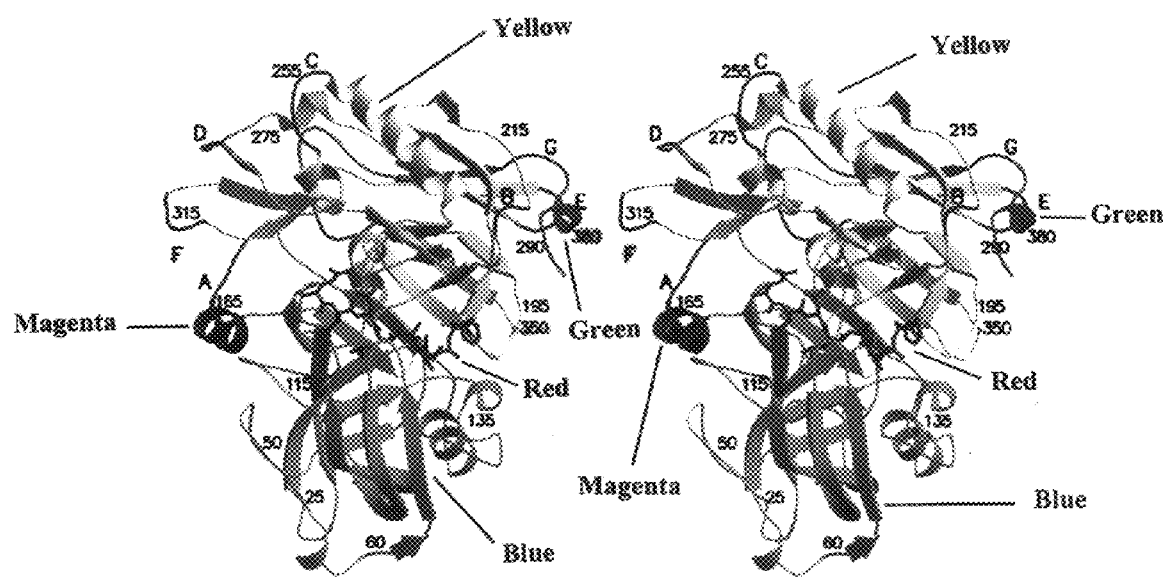
FIG. 6 is a stereo view of crystal structure of memapsin 2 protease domain with bound OM99-2. The polypeptide backbone of memapsin 2 is shown as a ribbon diagram. The N-lobe and C-lobe are blue and yellow, respectively, except the insertion loops (designated A to G, see FIG. 6) in the C-lobe are magenta and the C-terminal extension is green. The inhibitor bound between the lobes is shown in red.
Figure 7:
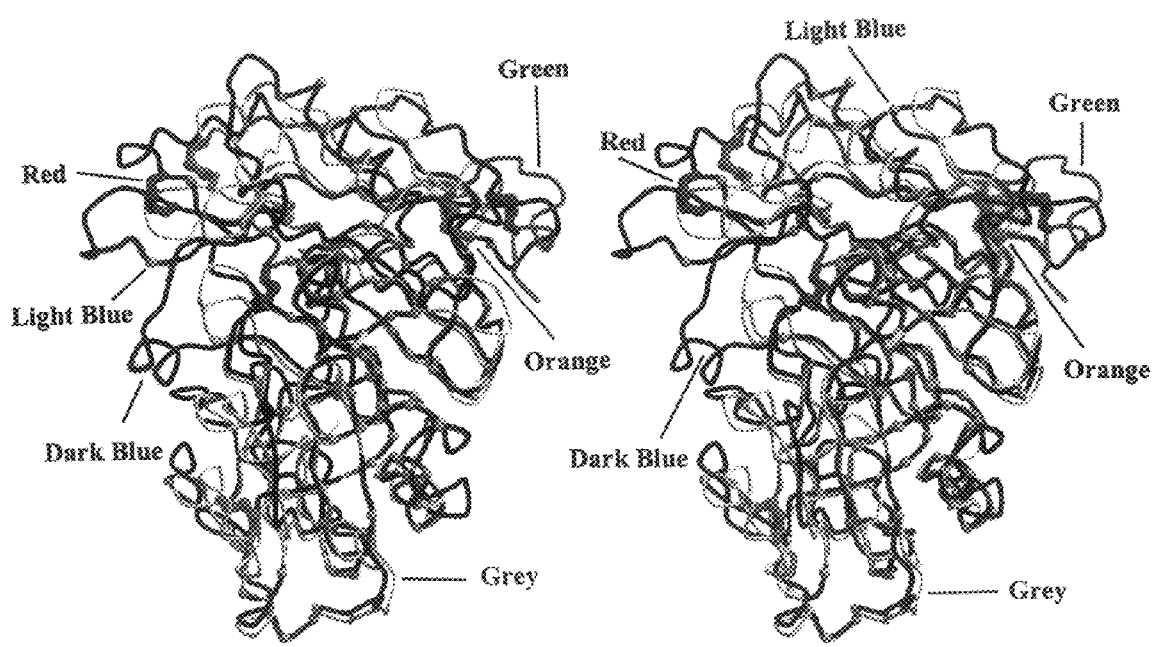
FIG. 7 is a stereo view of comparison of the three-dimensional structures of memapsin 2 and pepsin. The molecular surface of the former is significantly larger by the insertion of surface loops and helix and the C-terminal extension. Chain tracing of human memapsin 2 is dark blue and is grey for human pepsin. The light blue balls represent identical residues which are topologically equivalent. The disulfide bonds are shown in red for memapsin 2 and orange for pepsin. The C-terminal extension is in green.
Figure 8:
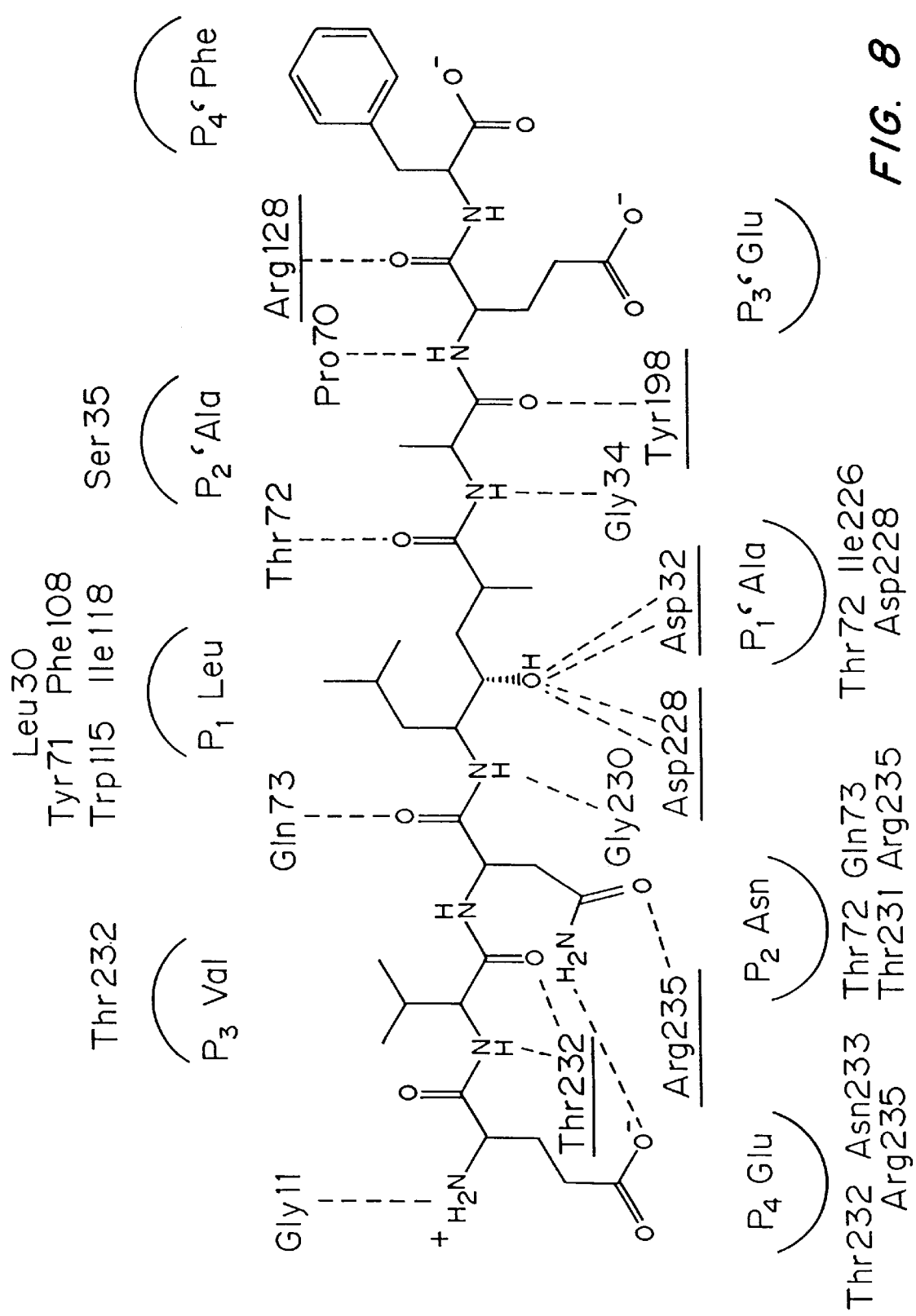
FIG. 8 is a schematic presentation of interaction between OM99-2 and memapsin 2 protease domain. The $S_3'$ and $S_4'$ subsites are not defined.

Compared to pepsin, the conformation of the N-lobe is essentially conserved (Sielecki et al., 1990). The most significant structural differences are the insertions and a C-terminal extension in the C-lobe. Four insertions in helices and loops (FIG. 6) are located on the adjacent molecular surface. Insertion F, which contains four acidic residues, is the most negatively charged surface on the molecule. Together, these insertions enlarged significantly the molecular boundary of memapsin 2 as compared to pepsin (FIG. 8). These surface structural changes may have function in the association of memapsin 2 with other cell surface components. Insertions B and E are located on the other side of the molecule (FIG. 6). The latter contains a beta-strand that paired with part of the C-terminal extension G. A six-residue deletion occurs at position 329 on a loop facing the flap on the opposite side of the active-site cleft, resulting in an apparently more accessible cleft. Most of the C-terminal extension (residues 359–393) is in highly ordered structure. Residues 369–376 form a beta structure with 7 hydrogen bonds to strand 293–299, while residues 378–383 form a helix (FIGS. 6 and 7). Two disulfide pairs (residues 155/359 and 217/382) unique to memapsin 2 fasten both ends of the extension region to the C-lobe. This C-terminal extension is much longer than those observed previously and is conformationally different [Cutfield, S. M., et al., Structure 3, 1261 (1995); Abad-Zapatero, C., et al., Protein Sci. 5, 640 (1996); Symersky, J. et al., Biochemistry 36, 12700 (1997); Yang, J., et al., Acta Crystallogr. D 55, 625 (1999)]. The last eight residues (386–393) are not seen in the electron density map; they may form a connecting stem between the globular catalytic domain and the membrane anchoring domain.

Of the 21 putative pro residues only the last six, 43p-48p, are visible in the electron density map. The remainders are likely mobile. Pro-memapsin expressed in mammalian cell culture has an N-terminus position at $Glu^{33}p$. However, an Arg-Arg sequence present at residues 43p–44p is a frequent signal for pro-protein processing, e.g., in prorenin (Corvol, P. et al., Hypertension 5, 13-9 (1983)). Recombinant memapsin 2 derived from this cleavage is fully active. The mobility of residues 28p–42p suggests that they are not part of the structure of mature memapsin 2.

MemaRsin 2-OM99-2 Interaction.

Figure 9:
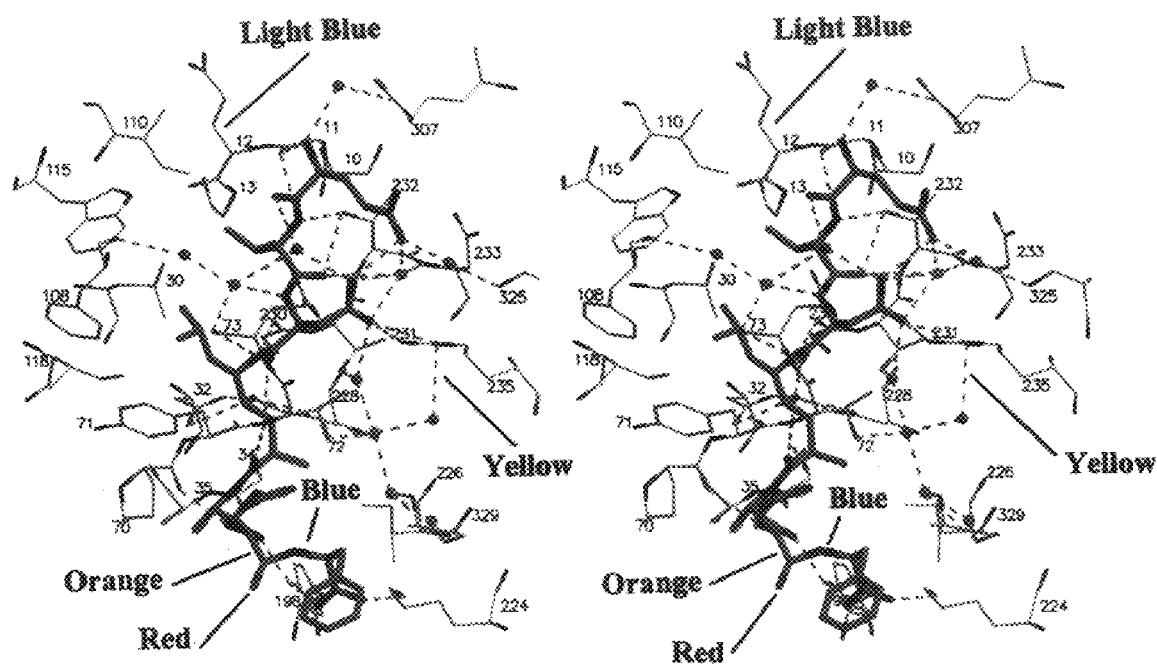
FIG. 9 is a stereo presentation of interactions between inhibitor OM99-2 (orange) and memapsin 2 (light blue). Nitrogen and oxygen atoms are marked blue and red, respectively. Hydrogen bonds are indicated in yellow dotted lines. Memapsin 2 residues which comprise the binding subsites are included. Residues $P_4$, $P_3$, $P_2$, $P_1$ and $P_1'$ (defined in FIG. 8) of OM99-2 are in an extended conformation. Inhibitor chain turns at residue P2' which makes a distinct kink at this position. The backbone of $P_3'$ and P4' directs the inhibitor to exit the active site.

The binding of the eight-residue inhibitor OM99-2 in the active-site cleft shares some structural features with other aspartic protease-inhibitor complexes [Davies, D. R., Annu. Rev. Biophys. Chem. 19, 189 (1990); Bailey and Cooper, (1994); Dealwis et al., (1994)]. These include four hydrogen bonds between the two active-site aspartics to the hydroxyl of the transition-state isostere, the covering of the flap (residues 69–75) over the central part of the inhibitor and ten hydrogen bonds to inhibitor backbone (FIGS. 8 and 9). Most of the latter are highly conserved among aspartic proteases [Davies, D. R. Annu. Rev. Biophys. Chem. 19, 189 (1990); Bailey and Cooper, (1994); Dealwis et al., (1994)] except that hydrogen bonds to $Gly^{11}$ and $Tyr^{198}$ are unique to memapsin 2. These observations illustrate that the manner by which memapsin 2 transition-state template for substrate peptide backbone and mechanism of catalysis are similar to other aspartic proteases. These common features are, however, not the decisive factors in the design of specific memapsin 2 inhibitors with high selectivity.

The observation important for the design of inhibitor drugs is that the memapsin 2 residues in contact with individual inhibitor side chains (FIG. 8) are quite different from those for other aspartic proteases. These side chain contacts are important for the design of tight binding inhibitor with high selectivity. Five N-terminal residues of OM99-2 are in extended conformation and, with the exception of $P_1$' Ala, all have clearly defined contacts (within 4 Å of an inhibitor side chain) with enzyme residues in the active-site cleft (FIG. 8).

The protease $S_4$ subsite is mostly hydrophilic and open to solvent. The position of inhibitor $P_4$ Glu side chain is defined by hydrogen bonds to $Gly^{11}$ and to $P_2$ Asn (FIG. 8) and the nearby sidechains of $Arg^{235}$ and $Arg^{307}$, which explains why the absence of this residue from OM99-2 cause a 10-fold increase in $K_i$. Likewise, the protease $S_2$ subsite is relatively hydrophilic and open to solvent. Inhibitor $P_2$ Asn side chain has hydrogen bonds to $P_4$ Glu and $Arg^{235}$. The relatively small $S_2$ residues $Ser^{325}$ and $Ser^{327}$ (Gin and Met respectively in pepsin) may fit a side chain larger than Asn. Memapsin 2 S1 and S3 subsites, which consist mostly of hydrophobic residues, have conformations very different from pepsin due to the deletion of pepsin helix hH2 (Dealwis, et al., (1994)). The inhibitor side chains of $P_3$ Val and $P_1$ Leu are closely packed against each other and have substantial hydrophobic contacts with the enzyme (FIG. 8), especially $P_3$ interacts with $Tyr^{71}$ and $Phe^{108}$. In the beta-secretase site of native APP, the $P_2$ and $P_1$ residues are Lys and Met respectively. Swedish mutant APP has Asn and Leu in these positions respectively, resulting in a 60-fold increase of $k_{cat}/K_m$ over that for native APP and an early onset of AD described by Mullan, M., et al. [Nat. Genet. 2, 340 (1992)]. The current structure suggests that inhibitor $P_2$ Lys would place its positively charge in an unfavorable interaction with $Arg^{235}$ with a loss of hydrogen bond to $Arg^{235}$, while $P_1$ Met would have less favorable contact with memapsin 2 than does leucine in this site (FIG. 9). No close contact with memapsin 2 was seen for $P_1$' Ala and an aspartic at this position, as in APP, may be accommodated by interacting with $Arg^{228}$.

The direction of inhibitor chain turns at $P_2$' and leads $P_3$' and $P_4$' toward the protein surface (FIG. 9). As a result, the side-chain position of $P_2$' Ala deviates from the regular extended conformation. The side chains of $P_3$' Glu and $P_4$' Phe are both pointed toward molecular surface with little significant interaction with the protease (FIG. 9). The relatively high B-factors (58.2 $Å^2$ for Glu and 75.6 $Å^2$ for Phe) and less well-defined electron density suggests that these two residues are relatively mobile, in contrast to the defined structure of the S3' and S4' subsites in renin-inhibitor (CH-66) complex (Dealwis et al., 1994). The topologically equivalent region of these renin subsites (residues 292–297 in pepsin numbering) is deleted in memapsin 2. These observations suggest that the conformation of three C-terminal residues of OM99-2 may be a functional feature of memapsin 2, possibly a way to lead a long protein substrate out of the active-site cleft.

EXAMPLE 10

Using The Crystal Structure to Design Inhibitors.

Pharmaceutically acceptable inhibitor drugs normally post a size limit under 800 daltons. In the case of memapsin 2 inhibitors, this requirement may even be more stringent due to the need for the drugs to penetrate the blood-brain barrier [Kearney and Aweeka, (1999)]. In the current model, well defined subsite structures spending $P_4$ to $P_2'$ provide sufficient template areas for rational design of such drugs. The spacial relationships of individual inhibitor side chain with the corresponding subsite of the enzyme as revealed in this crystal structure permits the design of new inhibitor structures in each of these positions. It is also possible to incorporate the unique conformation of subsites $P_2'$, $P_3'$ and $P_4'$ into the selectivity of memapsin 2 inhibitors. The examples of inhibitor design based on the current crystal structure are given below.

Figure 10:
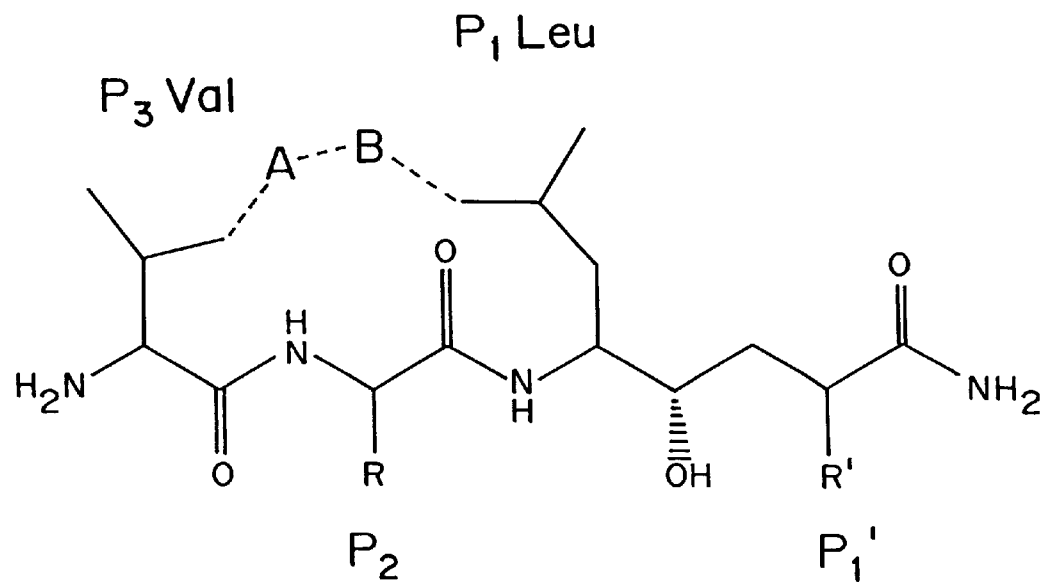
FIG. 10 are schematics of the cross linking between $P_3$ Val and $P_1$ Leu side chains in the design of new inhibitors for memapsin 2 based on the current crystal structure. R and R' at positions $P_2$ and $P_1'$ indicate amino acid side chains. Other structural elements of inhibitor are omitted for clarity.

Example A:

Since the side chains of P3 Val and $P_1$ Leu are packed against each other and there is no enzyme structure between them, cross-linking these side chains would increase the binding strength of inhibitor to memaspin 2. This is because when binding to the enzyme, the cross-linked inhibitors would have less entropy difference between the free and bound forms than their non-cross-linked counterparts [Khan, A. R., et al., Biochemistry, 37, 16839 (1998)]. Possible structures of the cross-linked side chains include those shown in FIG. 10.

Figure 11:
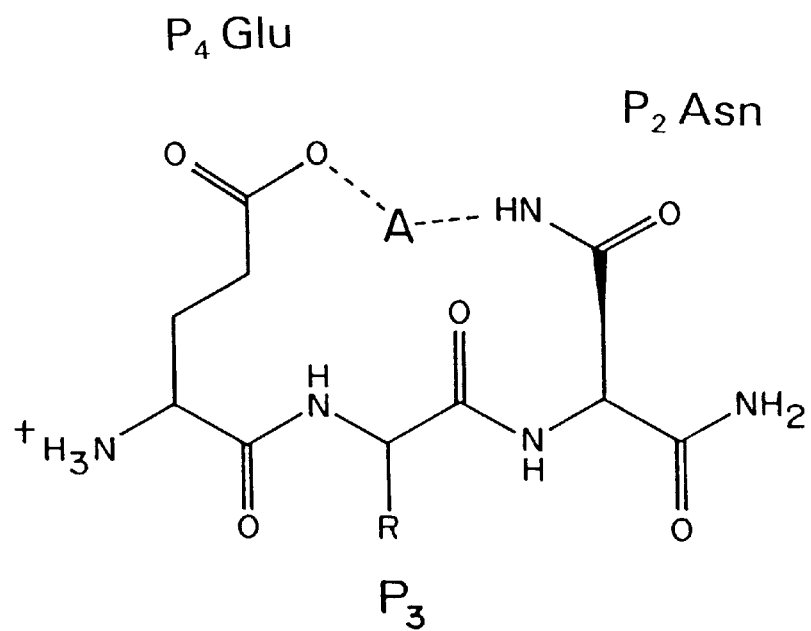
FIG. 11 are schematics of the cross linking between $P_4$ Glu and $P_2$ Asn side chains in the design of new inhibitors for memapsin 2 based on the current crystal structure. R at position $P_3$ indicates amino acid side chain. Other structural elements of inhibitor are omitted for clarity.

Example B:

The same situation exits between the P4 Glu and P2 Asn. The current crystal structure shows that these side chains are already hydrogen bonded to each other so the cross linking between them would also derive binding benefit as described in the Example A. The cross-linked structures include those shown in FIG. 11.

Figure 12:
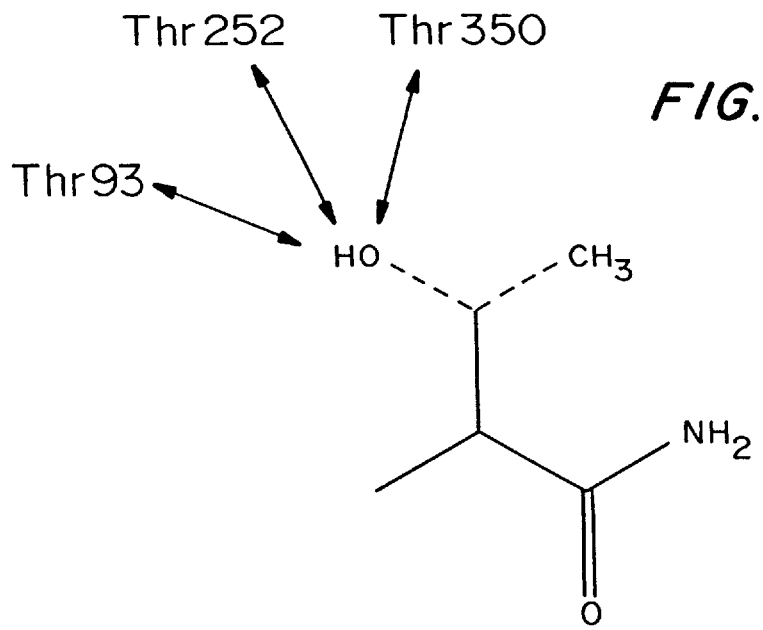
FIG. 12 is a schematic of the design for the side chain at the $P_1'$ subsite for the new memapsin 2 inhibitors based on the current crystal structure. Arrows indicate possible interactions between memapsin 2 and inhibitor. Other structural elements of inhibitor are omitted for clarity.

Example C:

Based on the current crystal structure, the P1' Ala side chain may be extended to add new hydrophobic, Van der Waals and H-bond interactions. An example of such a design is diagramed in FIG. 12.

Figure 13:
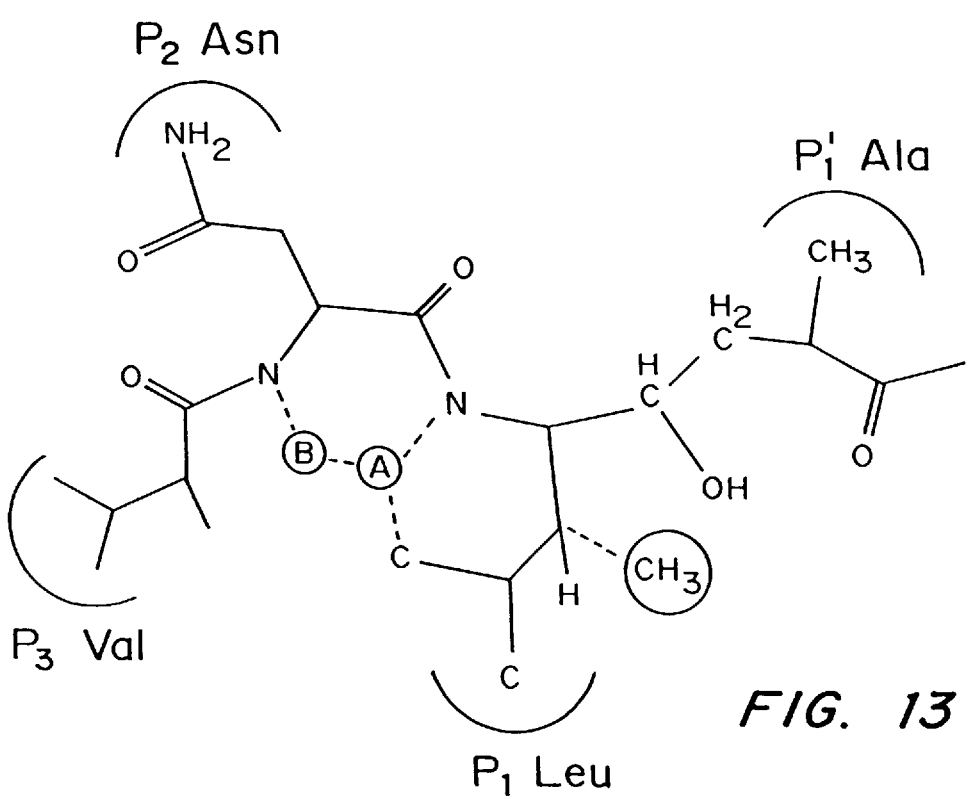
FIG. 13 is a schematic of the design of two six-membered rings in the inhibitor structure by the addition of atoms A and B. The ring formation involves the $P_1$-Leu side chain the the peptide backbone near $P_1$, $P_2$, and $P_3$. The new bonds are in dotted lines. A methyl group can be added to the beta-carbon of $P_1$-Leu. Other structural elements of inhibitor are omitted for clarity.

Example D:

Based on the current crystal structure, the polypeptide backbone in the region of P1, P2, and P3, and the side chain of P1-Leu can be bridged into rings by the addition of two atoms (A and B in FIG. 13). Also, a methyl group can be added to the beta-carbon of the P1-Leu (FIG. 13).

Modifications and variations of the methods and materials described herein will be obvious to those skilled in the art and are intended to come within the scope of the appended claims.

We claim:

1. A memapsin 2 protein consisting essentially of amino acid residues 16-456 of SEQ ID NO: 3, where in said memapsin protein is expressed in a bacterial cell and cleaves a β-secretase site of an amyloid precursor protein.

2. The memapsin 2 protein of claim 1, wherein the memapsin 2 protein is refolded after expression in the bacterial cell.

3. The memapsin 2 protein of claim 2, wherein the memapsin 2 protein is refolded by dissolution in a urea solution having a urea concentration of about 8M and at least one reducing agent at a pH of at least about pH 8.0.

4. The memapsin 2 protein of claim 3, wherein the memapsin 2 protein is refolded by dilution in an aqueous buffer having a pH of at least about pH 9, and wherein the pH subsequently is adjusted to about pH 8, and then maintained at a temperature of about 4° C. for a period of time in a range of between about 24 hours and about 48 hours.

5. The memapsin 2 of claim 3, wherein the memapsin 2 protein is refolded by dilution in an aqueous buffer having a pH of at least about pH 9 and including an oxidized and reduced glutathione, and wherein the urea concentration of the diluted solution of memapsin 2 protein decreases to about 4M, and wherein the pH is adjusted to about pH 8.

6. The memapsin 2 protein of claim 3, wherein the memapsin 2 protein is refolded by dissolution in urea having a urea concentration of about 8M and a pH of about pH 10, wherein a resulting solution subsequently is diluted in an aqueous buffer having a pH of about pH 9.0, and maintaining the solution at a temperature of about 4° C. for a period of time in a range of between about 24 hours and about 48 hours.

7. A crystallized memapsin 2 protein consisting essentially of amino acid residues 16-456 of SEQ ID NO: 3 and a substrate, wherein said memapsin 2 protein has a diffraction to at lest 3.5 Å or less.

8. The memapsin 2 of claim 7 having the parameters defined in Table 2.

9. The memapsin 2 of claim 7 having a diffraction to at least 2 Å or less.

10. The crystallized memapsin 2 protein of claim 7, wherein said memapsin 2 protein is bound to the substrate.

11. The memapsin 2 of claim 10, wherein the substrate includes a peptide.

12. The memapsin 2 of claim 11, wherein the peptide includes a transition state isostere.

13. The memapsin 2 of claim 12, wherein the transition state isostere has the formula A—CH(OH)—CH$_2$—B, where A and B are fragments of the peptide.

14. The memapsin 2 of claim 13, wherein the peptide is selected from the group consisting of OM99-1 and OM99-2.

15. The memapsin 2 of claim 14, wherein the β-secretase site includes an amino acid sequence of SEQ ID NO: 5.

16. The memapsin 2 of claim 10, wherein the substrate is a substrate that inhibits a memapsin 2 protein from cleaving the β-secretase site of an amyloid precursor protein.

17. The memapsin 2 of claim 16, wherein the β-secretase site includes an amino acid sequence of SEQ ID NO: 4.

18. The memapsin 2 protein of claim 7, wherein said memapsin 2 is expressed in a bacterial cell.

* * * * *

UNITED STATES PATENT AND TRADEMARK OFFICE
CERTIFICATE OF CORRECTION

PATENT NO. : 6,545,127 B1
DATED : April 8, 2003
INVENTOR(S) : Jordan J.N. Tang et al.

It is certified that error appears in the above-identified patent and that said Letters Patent is hereby corrected as shown below:

<u>Title page,</u>
Item [75], Inventors, add -- Arun K. Ghosh, River Forest, Il (US) --
Item [73], Assignee, add -- The Board of Trustees of the University of Illinois, Urbana, IL (US) --

Signed and Sealed this

Twelfth Day of August, 2003

JAMES E. ROGAN
*Director of the United States Patent and Trademark Office*